US006306627B1

United States Patent
Decker

(10) Patent No.: US 6,306,627 B1
(45) Date of Patent: Oct. 23, 2001

(54) ISOLATION OF THE BIOSYNTHESIS GENES FOR PSEUDO-OLIGOSACCHARIDES FROM STREPTOMYCES GLAUCESCENS GLA.O, AND THEIR USE

(75) Inventor: Heinrich Decker, Bremtal (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/194,905

(22) PCT Filed: May 30, 1997

(86) PCT No.: PCT/EP97/02826

§ 371 Date: Dec. 29, 1998

§ 102(e) Date: Dec. 29, 1998

(87) PCT Pub. No.: WO97/47748

PCT Pub. Date: Dec. 18, 1997

(30) Foreign Application Priority Data

Jun. 7, 1996 (DE) .............................................. 196 22 783

(51) Int. Cl.[7] .......................... C12P 19/00; C12P 21/06; C12N 9/00; C12N 1/20; C12N 15/00
(52) U.S. Cl. .......................... 435/72; 435/69.1; 435/183; 435/252.3; 435/320.1; 536/23.1
(58) Field of Search .................. 435/69.1, 72, 320.1, 435/183, 252.3; 536/23.2, 23.74

(56) References Cited

U.S. PATENT DOCUMENTS 5,753,501 * 5/1998 Crueger et al. .

FOREIGN PATENT DOCUMENTS 22 09 834 9/1973 (DE) .

0 730 029 9/1996 (DE) .

OTHER PUBLICATIONS

Stockmann, M. & Piepersberg, W., "Gene Probes for the Detection of 6–Deoxyhexose Metabolism in Secondary Meabolite–Producing Streptomycetes," FEMS Microbiology Letters, vol. 90, No. 2, (Jan. 1, 1992), pp. 185–190.

* cited by examiner

*Primary Examiner*—Ponnathapu Achutamurthy
*Assistant Examiner*—Manjunath N. Rao
(74) *Attorney, Agent, or Firm*—Heller Ehrman White & McAuliffe LLP

(57) ABSTRACT

The invention relates to a recombinant DNA molecule which comprises genes for biosynthesizing acarbose and homologous pseudo-oligosaccharides; to oligonucleotide primers for the PCR amplification of the molecule; to proteins which can be obtained by expressing the genes located on a molecule; to vectors and host cells which comprise the above-mentioned DNA molecule; to proteins which are encoded by the DNA molecule; to proteins which are expressed by means of said vectors in said host cells; to processes for preparing acarbose by introducing the characterized genes into appropriate host organisms and/or eliminating these genes from the host organisms; to processes for completing the gene cluster of genes for biosynthesizing acarbose, to processes for isolating analogous gene clusters in organisms other than *Streptomyces glaucescens* GLA.O, to processes for mutating promoters of endogenous acarbose biosynthesis genes for the purpose of increasing the yield of acarbose, to the use of *Streptomyces glaucescens* GLA.O for preparing acarbose and for preparing mutants of *Streptomyces glaucescens* GLA.O which are optimized with regard to the acarbose yield.

26 Claims, 5 Drawing Sheets

Fig. 1: Southern hybridization using *Streptomyces glaucescens* GLA.O
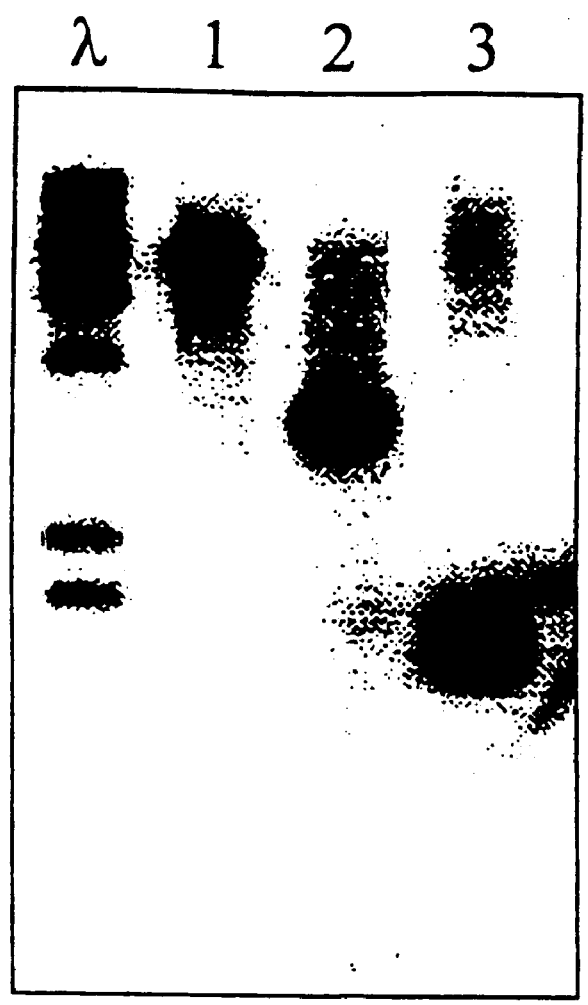

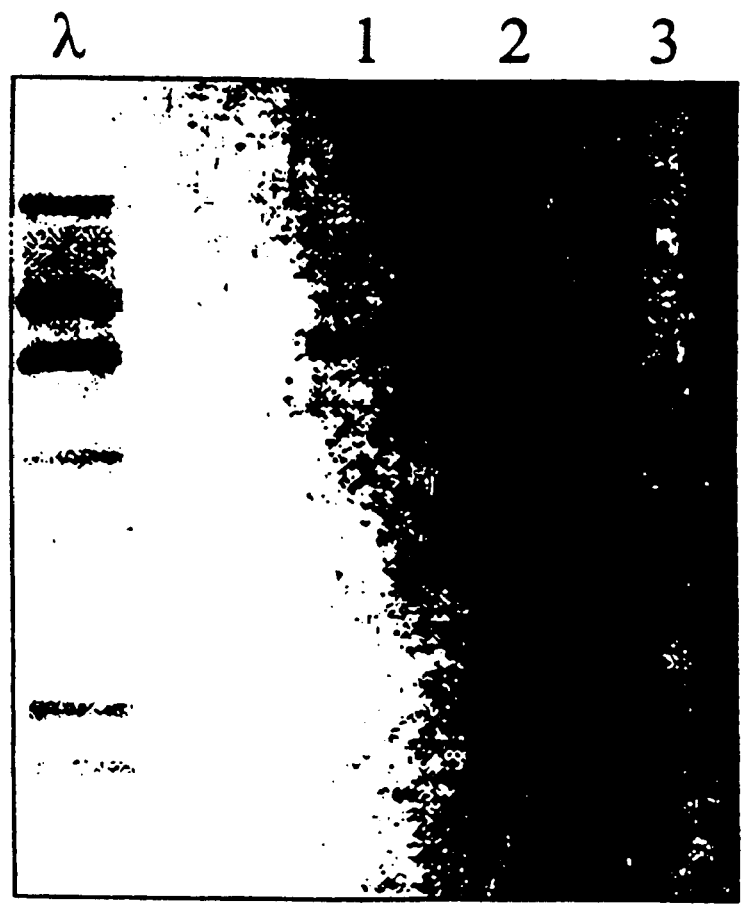
Fig. 2: Southern hybridization using *Streptomyces glaucescens* GLA.O

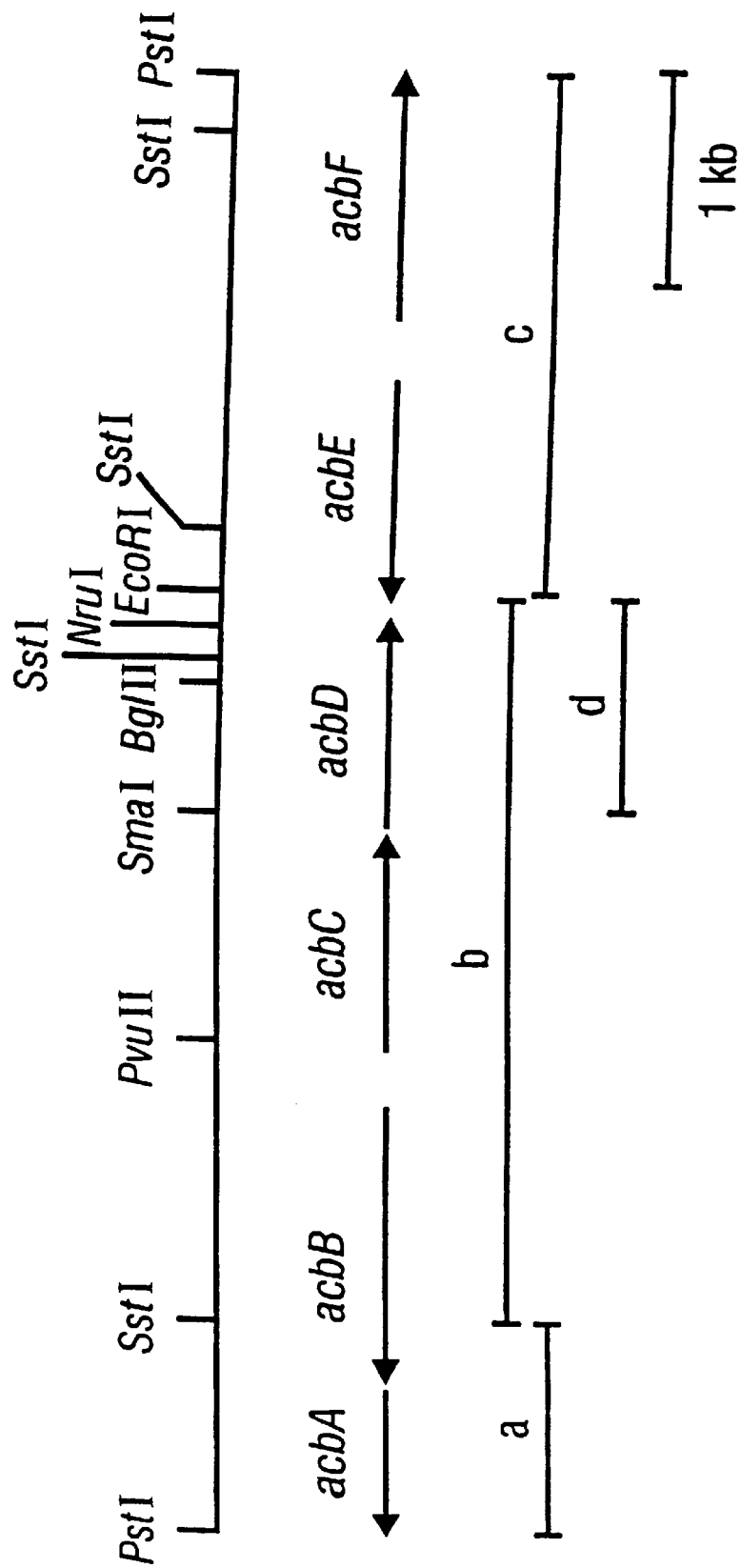
Fig. 3: Restriction map of the 6.8 kb PstI fragment from *Streptomyces glaucescens* GLA.O

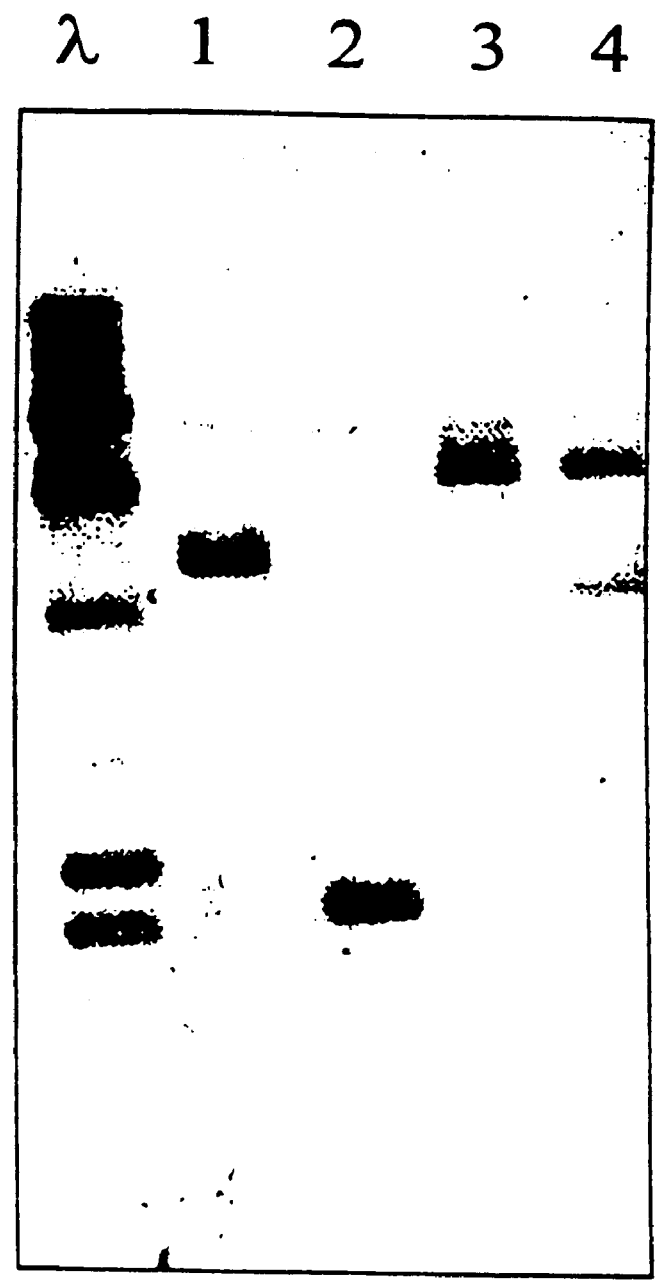
Fig. 4: Southern hybridization using *Streptomyces glaucescens* Δacb

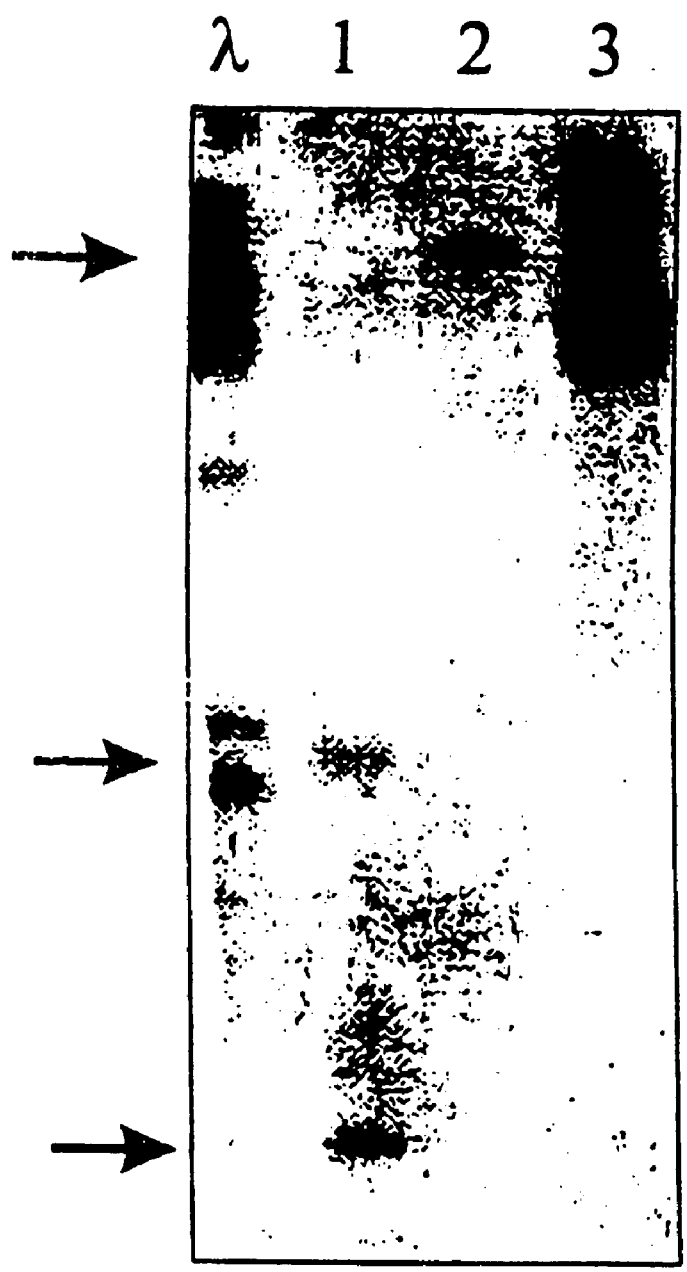
Fig. 5: Southern hybridization using *Actinoplanes* sp. SE50/100

ISOLATION OF THE BIOSYNTHESIS GENES FOR PSEUDO-OLIGOSACCHARIDES FROM STREPTOMYCES GLAUCESCENS GLA.O, AND THEIR USE

The present invention relates to the isolation of genes which encode enzymes for the biosynthesis of α-amylase inhibitors, so-called pseudo-oligosaccharides. The genes concerned are, in particular, genes from the Streptomycetes strain *Streptomyces glaucescens* GLA.O (DSM 40716). In addition, this present patent describes the use of these genes for producing acarbose and homologous substances with the aid of *Streptomyces glaucescens* GLA.O, the heterologous expression of these genes in other strains which produce pseudo-oligosaccharides (e.g. Actinoplanes sp SE50/100) for the purpose of increasing and stabilizing production, and also their heterologous expression in other microorganisms such as *E. coli, Bacillus subtilis*, Actinomycetales, such as Streptomyces, Actinoplanes, Ampullariella and Streptoporangium strains, *Streptomyces hygroscopicus var. limoneus* and *Streptomyces glaucescens*, and also biotechnologically relevant fungi (e.g. *Aspergillus niger* and *Penicillium chrysogenum*) and yeasts (e.g. *Saccharomyces cerevisiae*). The invention also relates to homologous genes in other microorganisms and to methods for isolating them.

*Streptomyces glaucescens* GLA.O produces the two antibiotics hydroxystreptomycin (Hütter (1967) Systematik der Streptomyceten (Taxonomy of the Streptomycetes). Basel, Karger Verlag) and tetracenomycin (Weber et al. (1979) Arch. Microbiol. 121: 111–116). It is known that streptomycetes are able to synthesize structurally varied natural products. However, the conditions under which these compounds are produced are frequently unknown, or else the substances are only produced in very small quantities and not detected.

The α-amylase inhibitor acarbose has been isolated from a variety of Actinoplanes strains (SE50, SE82 and SE18) (Schmidt et al. (1977) Naturwissenschaften 64: 535–536). This active substance was discovered in association with screening for (α-amylase inhibitors from organisms of the genera Actinoplanes, Ampullariella and Streptosporangium. Acarbose is pseudotetrasaccharide which is composed of an unusual unsaturated cyclitol unit to which an amino sugar, i.e. 4,6-dideoxy-4-amino-D-glucopyranose, is bonded. Additional (α-1,4-glycosidically linked D-glucopyranose units can be bonded to the amino sugar. Thus, acarbose, for example, contains two further molecules of D-glucose. The producing strain synthesizes a mixture of pseudo-oligosaccharide products which possess sugar side chains of different lengths (Schmidt et al. (1977) Naturwissenschaften 64: 535–536). The acarbose cyclitol residue is identical to the compound valienamine, which is a component of the antibiotic validamycin A (Iwasa et al. (1979) J. Antibiot. 32: 595–602) from *Streptomyces hygroscopicus var. limoneus*.

Acarbose can be produced by fermentation using an Actinoplanes strain and has achieved great economic importance as a therapeutic agent for diabetics. While Actinoplanes synthesizes a mixture of α-amylase inhibitor products, it is only the compound having the relative molecular weight of 645.5 (acarviosin containing 2 glucose units (Truscheit (1984) Vlilth International Symposium on Medicinal Chemistry, Proc. Vol. 1. Swedish Academy of Pharmaceutical Sciences, Stockholm, Sweden), which is employed under the generic name of acarbose. The fermentation conditions are selected to ensure that acarbose is the main product of the fermentation. Alternatives are to use particular selectants and strains in which acarbose is formed as the main product or to employ purification processes for achieving selective isolation (Truscheit (1984) VlIIth International Symposium on Medicinal Chemistry, Proc. Vol. 1. Swedish Academy of Pharmaceutical Sciences, Stockholm, Sweden). It is also possible to transform the product mixture chemically in order, finally, to obtain the desired product acarbose.

In contrast to the genus Streptomyces, the genus Actinoplanes has not so far been investigated intensively from the genetic point of view. Methods which were established for the genus Streptomyces are not transferable, or are not always transferable, to the genus Actinoplanes. In order to use molecular biological methods to optimize acarbose production in a purposeful manner, the genes for acarbose biosynthesis have to be isolated and characterized. In this context, the possibility suggests itself of attempting to set up a host/vector system for Actinoplanes sp. However, this is very tedious and elaborate owing to the fact that studies on Actinoplanes have been relatively superficial.

The invention described in the present patent application achieves the object of cloning the biosynthesis genes for acarbose and homologous pseudo-oligosaccharides, with these genes being cloned from *Streptomyces glaucescens* GLA.O, which is a streptomycete which has been thoroughly investigated genetically (Crameri et al. (1983) J. Gen. Microbiol. 129: 519–527; Hintermann et al. (1984) Mol. Gen. Genet. 196: 513–520; Motamedi and Hutchinson (1987) PNAS USA 84: 4445–4449; Geistlich et al. (1989) Mol. Microbiol. 3: 1061–1069) and which, surprisingly, is an acarbose producer. In starch-containing medium, *Streptomyces glaucescens* GLA.O produces pseudo-oligosaccharides having the molecular weights 645, 807 and 970.

Part of the subject matter of the invention is, therefore, the isolation of the corresponding biosynthesis genes from *Streptomyces glaucescens* GLA.O and their use for isolating the adjoining DNA regions in order to complete the gene cluster of said biosynthesis genes.

The isolation of the genes for biosynthesizing pseudo-oligosaccharides, and the characterization of these genes, are of great importance for achieving a better understanding of the biosynthesis of the pseudo-oligosaccharides and its regulation. This knowledge can then be used to increase the productivity of the *Streptomyces glaucescens* GLA.O strain with regard to acarbose production by means of established classical and molecular biological methods. In addition to this, the entire gene cluster which encodes the synthesis of the pseudo-oligosaccharides, or individual genes from this gene cluster, can also be expressed in other biotechnologically relevant microorganisms in order to achieve a further increase in, or a simplification of, the preparation of pseudo-oligosaccharides such as acarbose. Specific modification of the biosynthesis genes can also be used to prepare a strain which exclusively produces acarbose having a molecular weight of 645. Since the genes for biosynthesizing antibiotics are always present in clusters and are often very strongly conserved (Stockmann and Piepersberg (1992) FEMS Microbiol. Letters 90: 185–190; Malpartida et al. (1987) Nature 314:642–644), the *Streptomyces glaucescens* GLA.O genes can also be used as a probe for isolating the acarbose-encoding genes from Actinoplanes sp., for example. The expression of regulatory genes, or of genes which encode limiting steps in the biosynthesis, can result in productivity in *Streptomyces glaucescens* GLA.O, Actinoplanes sp. or corresponding producer strains being increased. An increase in productivity can also be achieved by switching off (knocking out or mutagenizing) those acarbose biosynthesis genes which have an inhibitory effect in the biosynthesis.

One possible strategy for cloning antibiotic biosynthesis genes which have not previously been isolated is that of using gene-specific probes (Stockmann and Piepersberg (1992) FEMS Microbiol. Letters 90: 185–190; Malpartida et al. (1987) Nature 314:642–644). These probes can be DNA fragments which are $P^{32}$-labeled or labeled in some other way; otherwise, the appropriate genes can be amplified directly from the strains to be investigated using degenerate PCR primers and isolated chromosomal DNA as the template.

The latter method has been employed in the present study. Pseudo-oligosaccharides such as acarbose contain a 4,6-deoxyglucose building block as a structural element. The enzyme dTDP-glucose 4,6-dehydratase is known to be involved in the biosynthesis of 4,6-deoxyglucose (Stockmann and Piepersberg (1992) FEMS Microbiol, Letters 90: 185–190). Since deoxysugars are a frequent constituent of natural products and antibiotics, this enzyme may possibly be a means for isolating the corresponding antibiotic biosynthesis genes. Since these genes are always present as clusters, it is sufficient to initially isolate one gene; the isolation and characterization of the adjoining DNA regions can then be undertaken subsequently.

For example a dTDP-glucose 4,6-dehydratase catalyzes a step in the biosynthesis of hydroxystreptomycin in *Streptomyces glaucescens* GLA.O (Retzlaff et al. (1993) Industrial Microorganisms. Basic and applied molecular genetics ASM, Washington D.C., USA). Further dTDP-glucose 4,6-dehydratases have been isolated from other microorganisms, for example from *Streptomyces griseus* (Pissowotzki et al. (1991) Mol. Gen. Genet. 231: 113–123), *Streptomyces fradiae* (Merson-Davies and Cundcliffe (1994) Mol. Microbiol. 13: 349–355) and *Streptomyces violaceoruber* (Bechthold, et al. (1995) Mol. Gen. Genet. 248: 610–620).

It was consequently possible to deduce the sequences for the PCR primers for amplifying a dTDP-glucose 4,6-dehydratase from the amino acid sequences of already known biosynthesis genes. For this, conserved regions in the protein sequences of these enzymes were selected and the amino acid sequences were translated into a nucleic acid sequence in accordance with the genetic code. The protein sequences were taken from the EMBL and Genbank databases. The following sequences were used: *Streptomyces griseus*; accession number: X62567 gene: strE (dated 10.30.1993); *Streptomyces violaceoruber*; accession number: L37334 gene: graE (dated 04.10.1995); *Saccharopolyspora etythraea*; accession number: L37354 gene: gdh (dated 11.09.1994). A large number of possible primer sequences are obtained as a result of the degeneracy of the genetic code. The fact that streptomycetes usually contain a G or C in the third position of a codon (Wright and Bibb (1992) gene 113: 55–65) reduces the number of primers to be synthesized. These primer mixtures can then be used to carry out a PCR amplification with the DNA from strains to be investigated, with the amplification ideally leading to an amplified DNA fragment. In the case of highly conserved proteins, this fragment is of a predictable length which ensues from the distance between the primers in the nucleic acid sequence of the corresponding gene. However, an experimental mixture of this nature does not inevitably have to result in an amplificate. The primers may be too unspecific and amplify a very large number of fragments; alternatively, no PCR product is obtained it there are no complementary binding sites in the chromosome for the PCR primers which have been prepared.

The investigation of the streptomycete strain *Streptomyces glaucescens* GLA.O resulted in an amplified DNA fragment (acbD) which had the expected length of 550 bp. Further investigation showed that, besides containing a dTDP-glucose 4,6-dehydratase gene for biosynthesizing hydroxystreptomycin, this strain surprisingly contains a second dTDP-glucose 4,6-dehydratase gene for biosynthesizing pseudo-oligo-saccharides such as acarbose. While the two genes exhibit a high degree of homology, they are only 65% identical at the amino acid level. The acbD probe (see Example 2 and Table 2A) was used to isolate, from *Streptomyces glaucescens* GLA.O, a 6.8 kb PstI DNA fragment which encodes a variety of genes (acbA, acbB, acdC, acbD, acbE and acbF) which are involved in the biosynthesis of the pseudo-oligosaccharides. Deleting the acbBCD genes (aminotransferase, acbB, dTDP-glucose synthase, acbC, dTDP-glucose 4,6-dehydratase, acbD, see Example 6) resulted in the production of a mutant of *Streplomyces glaucescens* GLA.O which no longer produces any pseudo-oligosaccharides in the production medium. The involvement of the acbBCD genes in the synthesis of pseudo-oligosaccharides was therefore verified by deleting the corresponding loci.

The two genes, i.e. dTDP-glucose synthase and dTDP-glucose 4,6-dehydratase, ought to be involved in the biosynthesis of the deoxysugar of the pseudo-oligosaccharides, as can be concluded from the function of thoroughly investigated homologous enzymes (see above). The aminotransferase (encoded by the acbB gene) is probably responsible for transferring the amino group either to the sugar residue or to the cyclitol residue. By analyzing the protein sequence of acbB, an amino acid motif was found which is involved in binding pyridoxal phosphate. This motif is typical of class III aminotransferases (EC 2.6.1.11; EC 2.6.1.13; EC 2.6.1.18; EC 2.6.1.19; EC 2.6.1.62; EC 2.6.1.64; EC 5.4.3.8). The precise enzymic function of acbB can only be elucidated by further investigation of the biosynthesis of the pseudo-oligosaccharides. acbE encodes a transcription-regulating protein which exhibits a great deal of similarity to DNA-binding proteins which possess a helix-turn-helix motif (e.g. *Bacillus subtilis* DegA, P37947: Swiss-Prot database). Thus, the transcription activator CcpA from *Bacillus subtilis* inhibits the formation of α-amylase in the presence of glucose, for example (Henkin et al. (1991) Mol. Microbiol. 5: 575–584). Other representatives of this group are proteins which recognize particular sugar building blocks and are able to exhibit a positive or negative effect on the biosynthesis of metabolic pathways. The biosynthesis of the pseudo-oligosaccharides is also regulated in *Streptomyces glaucescens* GLA.O. It was only previously possible to demonstrate the synthesis of pseudo-oligosaccharides on starch-containing media. While this method indicated that AcbE might be responsible for regulating pseudo-oligosaccharide synthesis, the precise mechanism is still not known. However, molecular biological methods can now be used to modify the gene specifically in order to obtain an increased rate of pseudo-oligosaccharide biosynthesis. Furthermore, the DNA site at which acbE binds can be identified by means of so-called gel shift assays (Miwa et al. (1994) Microbiology 140: 2576–2575). An increase in the rate at which acarbose is biosynthesized can be achieved after identifying and then modifying the promoters and other regulatory DNA regions which are responsible for the transcription of the pseudo-oligosaccharide genes.

At present, the function of acbF is still not definitely known. The corresponding gene product exhibits homologies with sugar-binding proteins such as the sugar-binding protein from *Streptococcus mutans* (MsmE; Q00749: Swissprot database), making it probable that it is involved in the biosynthesis of the pseudo-oligosaccharides. The gene product of the acbA gene exhibits homologies with known bacterial ATP-binding proteins (e.g. from *Streptomyces peucitus* DrrA, P32010: SwissProt database). The AcbA protein possesses the typical ATP/GTP binding motif, i.e. the so-called P loop. These proteins constitute an important component of so-called ABC transporters, which are involved in the active transport of metabolites at biological membranes (Higgins (1995) Cell 82: 693–696). Accordingly, AcbA could be responsible for exporting pseudo-oligosaccharides out of the cell or be involved in importing sugar building blocks for biosynthesizing α-amylase inhibitors such as maltose.

All streptomycete genes for biosynthesizing secondary metabolites which have so far been analyzed are arranged in a cluster. For this reason, it is to be assumed that the acarbose biosynthesis genes according to the application are also arranged in such a gene cluster. The remaining genes which are relevant for pseudo-oligosaccharide biosynthesis can therefore also be isolated by isolating the DNA regions which adjoin the 6.8 kb PstI DNA fragment according to the invention. As has also already been mentioned above, it is readily possible to isolate homologous gene clusters from microorganisms other than *Streptomyces glaucescens* GLA.O.

The invention therefore relates to a recombinant DNA molecule which comprises genes for biosynthesizing acarbose and homologous pseudo-oligosaccharides, in particular a recombinant DNA molecule in which individual genes are arranged, with respect to their direction of transcription and order, as depicted in FIG. 3 and/or which exhibits a restriction enzyme cleavage site pattern as depicted in FIG. 3, and, preferably, to a recombinant DNA molecule which (a) comprises a DNA sequence according to Table 4, or parts thereof;

(b) comprises a DNA sequence which is able to hybridize, under stringent conditions, with the DNA molecule according to (a), or parts thereof; or (c) comprises a DNA sequence which, because of the degeneracy of the genetic code, differs from the DNA molecules according to (a) and (b) but which permits the expression of the proteins which can be correspondingly expressed using the DNA molecule according to (a) and (b), or parts thereof.

The invention furthermore relates to a recombinant DNA molecule which comprises the acbA gene, in particular which is characterized in that it comprises the DNA sequence of nucleotides 1 to 720 according to Table 4, or parts thereof; to a recombinant DNA molecule which comprises the acbB gene, in particular which is characterized in that it comprises the DNA sequence of nucleotides 720 to 2006 according to Table 4, or parts thereof; to a recombinant DNA molecule which comprises the acbC gene, in particular which is characterized in that it comprises the DNA sequence of nucleotides 2268 to 3332 according to Table 4, or parts thereof; to a recombinant DNA molecule which comprises the acbD gene, in particular which is characterized in that it comprises the DNA sequence of nucleotides 3332 to 4306 according to Table 4, or parts thereof; to a recombinant DNA molecule which comprises the acbE gene, in particular which is characterized in that it comprises the DNA sequence of nucleotides 4380 to 5414 according to Table 4, or parts thereof; and to a recombinant DNA molecule which comprises the acbF gene, in particular which is characterized in that it comprises the DNA sequence of nucleotides 5676 to 6854 according to Table 4, or parts thereof.

The invention furthermore relates to oligonucleotide primers for the PCR amplification of a recombinant DNA molecule which is as described above and which comprises genes for biosynthesizing acarbose and homologous pseudo-oligosaccharides, with the primers having, in particular, the sequence according to Table 1.

The invention furthermore relates to a vector which comprises a recombinant DNA molecule which comprises a DNA molecule as described in the penultimate and prepenultimate paragraphs, in particular which is characterized in that the vector is an expression vector and said DNA molecule is linked operatively to a promoter sequence, with the vector preferably being being suitable for expression in host organisms which are selected from the group consisting of *E. coli, Bacillus subtilis*, Actinomycetales, such as *Streptomyces, Actinoplanes, Ampullariella* and *Streptosporangium* strains, *Streptomyces hygroscopicus var. limoneus, Streptomyces glaucescens* and also biotechnologically relevant fungi (e.g. *Aspergillus niger, Penicillium chrysogenum*) and yeasts (e.g. *Saccharomyces cerevisiae*), with *Streptomyces glaucescens* GLA.O or Actinoplanes sp. being very particularly preferred. Since the operative linkage of said DNA molecule to promoter sequences of the vector is only one preferably embodiment of the invention, it is also possible for expression to be achieved using promoter sequences which are endogenous in relation to the DNA molecule, e.g. the promoters which are in each case natural, or the natural promoters which have been mutated with regard to optimizing the acarbose yield. Such natural promoters are part of the DNA molecule according to the invention.

The invention furthermore relates to a vector which comprises a DNA molecule according to the invention for use in a process for eliminating or altering natural acarbose biosynthesis genes in an acarbose-producing microorganism. Such a vector is preferably selected from the group consisting of pGM160 and vectors as described in European Patents EP 0 334 282 and EP 0 158 872.

The invention furthermore relates to a host cell which is transformed with one of the above-described DNA molecules or vectors, in particular characterized in that said host cell is selected from the group consisting of *E. coli, Bacillus subtilis*, Actinomycetales, such as *Streptomyces, Actinoplanes, Ampullariella* or *Streptosporangium* strains, *Streptomyces hygroscopicus var. limoneus* or *Streptomyces glaucescens*, and also biotechnologically relevant fungi (e.g. *Aspergillus niger* and *Penicillium chrysogenum*) and yeasts (e.g. *Saccharorryces cerevisiae*); it is very particularly preferred for it to be selected from the group consisting of *Streptomyces glaucescens* GLA.O and Actinoplanes sp.

The invention furthermore relates to a protein mixture which can be obtained by expressing the genes of the recombinant DNA molecule according to the invention, comprising genes for biosynthesizing acarbose and homologous pseudo-oligosaccharides, ii particular characterized in that the DNA molecule (a) comprises a DNA sequence according to Table 4, or parts thereof;

(b) comprises a DNA sequence which is able to hybridize, under stringent conditions, with the DNA molecule according to (a) or parts thereof; or (c) comprises a DNA sequence which, because of the degeneracy of the genetic code, differs from the DNA molecules according to (a) and (b) but which permits the expression of the proteins which can correspondingly be expressed using the DNA molecule according to (a) and (b), or parts thereof.

The invention furthermore relates to isolated proteins which can be obtained by expressing the genes which are encoded by the DNA molecule described in the previous paragraph.

The following statements apply to all the individual genes identified within the context of the present invention and have only been brought together for reasons of clarity: the invention furthermore relates to a protein which is encoded by a recombinant DNA molecule as described in the last paragraph but one, in particular characterized in that it comprises the DNA sequence of nucleotides 1 to 720 or 720 to 2006 or 2268 to 3332 or 3332 to 4306 or 4380 to 5414 or 5676 to 6854 according to Table 4 or parts thereof; a protein is very particularly preferred which is enoded by the acbA gene or the acbB gene or the acbc gene or the acbD gene or the acbE gene or the acbf gene, and which comprises the amino acid sequence according to Table 4 or parts thereof.

The invention furthermore relates to a process for obtaining the proteins which were described above as being part of the subject-matter of the invention, which process is characterized in that (a) the proteins are expressed in a suitable host cell, in particular which is characterized in that said host cell is selected from the group consisting of *E. coli, Bacillus subtilis*, Actinomycetales, such as *Streptomyces, Actinoplanes, Ampullariella* or *Streptosporangium* strains, *Streptomyces, hygroscopicus var. limoneus* or *Streptomyces glaucescens*, and also biotechnologically relevant fungi (e.g. *Aspergillus niger* and *Penicillium chrysogenum*) and yeasts (e.g. *Saccharomyces cerevisiae*); with the host cell very particularly preferably being selected from the group consisting of *Streptomyces glaucescens* GLA.O and Actinoplanes sp., and (b) are isolated.

The invention furthermore relates to a process for preparing acarbose, characterized in that (a) one or more genes of the recombinant DNA molecule which comprises a DNA sequence according to Table 4 or parts thereof or which comprises a DNA sequence which is able to hybridize, under stringent conditions, with the DNA molecule according to Table 4, or parts thereof, or which comprises a DNA sequence which, because of the degeneracy of the genetic code, differs from the DNA molecules which have just been described but which permits the expression of the proteins which can be correspondingly expressed using these DNA molecules, or parts thereof, is/are used for expression in a suitable host cell which is selected, in particular, from the same group as in the last paragraph, and (b) the acarbose is isolated from culture supernatants of said host cell.

The invention furthermore relates to a process for preparing acarbose, characterized in that (a) one or more genes of the recombinant DNA molecule which comprises a DNA sequence according to Table 4 or parts thereof or which comprises a DNA sequence which is able to hybridize, under stringent conditions, with the DNA molecule according to Table 4, or parts thereof, or which comprises a DNA sequence which, because of the degeneracy of the genetic code, differs from the DNA molecules which have just been described but which permits expression of the proteins which can be correspondingly expressed using the DNA molecules, or parts thereof, are eliminated in an acarbose-producing host cell, in particular *Streptomyces glaucescens* GLA.O and Actinoplanes sp., and (b) the acarbose is isolated from said host cell.

In this connection, the elimination of one or more genes can be effected by means of standard molecular biological methods, for example using the above-described vectors (pGM160 and others). A gene to be eliminated could, for example, be the acbE gene, which probably has a regulatory function. Genes could likewise be eliminated with the aim of obtaining pure acarbose as the only fermentation product and no longer obtaining a mixture of homologous pseudo-oligosaccharides (see above). The elimination of said genes is preferably achieved using the vectors which have been described above for this purpose.

The invention furthermore relates to a process for preparing acarbose, characterized in that the processes for preparing acarbose which have been described in the previous two paragraphs are combined with each other, such that, therefore, one or more of said genes is/are expressed artificially and one or more of said genes is/are eliminated.

The invention furthermore relates to a process for altering the gene expression of endogenous acarbose biosynthesis genes by mutating the respective gene promoter in order to obtain improved yields of acarbose. In this context, known methods of homologous recombination can be used to introduce the mutations into the production strain to be improved. These mutations can be transitions, deletions and/or additions. An "addition" can, for example, denote the addition of one single nucleotide or several nucleotides or of one or more DNA sequences which have a positive regulatory effect and which bring about an enhancement of the expression of an endogenous gene for biosynthesizing acarbose. The converse case, i.e. the addition of a DNA sequence which has a negative regulatory effect for repressing an endogenous acarbose biosynthesis gene is also a preferred form of an addition. "Transitions" may, for example, be nucleotide exchanges which reduce or amplify the effect of regulatory elements which act negatively or positively. "Deletions" can be used to remove regulatory elements which act negatively or positively. The endogenous genes of this process are preferably present in Actinomycelales, such as *Streptomyces, Actinoplanes, Ampullariella* or *Streptosporangium* strains, *Streptomyces hygroscopicus var. limoneus* or *Streptomyces glaucescens*; very particularly, they are present in *Streptomyces glaucescens* GLA.O and Actinoplanes sp.

The invention furthermore relates to the use of *Streptomyces* GLA.O for obtaining acarbose.

The invention furthermore relates to the use of *Streptomyces* GLA.O for preparing mutants of this strain by the "classical route", which mutants make it possible to achieve a more abundant production of acarbose. The methods for preparing improved natural product producers of this nature have been known for a long time and frequently make use of classical steps of mutagenesis and selection.

The invention furthermore relates to a process for completing the gene cluster for biosynthesizing acarbose and homologous polysaccharides according to Table 4, characterized in that a) hybridization probes which are derived from the DNA molecule according to Table 4 are prepared, b) these hybridization probes are used for the genomic screening of DNA libraries obtained from *Streptomyces glaucescens* GLA.O, and c) the clones which are found are isolated and characterized.

The invention furthermore relates to a process for completing the gene cluster for biosynthesizing acarbose and homologous pseudo-oligosaccharides according to Table 4, characterized in that, proceeding from the recombinant DNA molecule according to Table 4, a) PCR primers are prepared,
b) these PCR primers are used to accumulate DNA fragments of genomic DNA from *Streptomyces glaucescens* GLA.O, with these primers being combined with those primers which hybridize from sequences of the vector system employed,
c) the accumulated fragments are isolated and characterized.

The invention furthermore relates to a process for isolating a gene cluster for biosynthesizing acarbose and homologous pseudo-oligosaccharides from acarbose-producing microorganisms other than *Streptomyces glaucescens* GLA.O, characterized in that, proceeding from the recombinant DNA molecule according to claim 4, a) hybridization probes are prepared,
b) these hybridization probes are used for the genomic or cDNA screening of DNA libraries which have been obtained from the corresponding microorganism, and
c) the clones which are found are isolated and characterized.

The invention furthermore relates to a process for isolating a gene cluster for biosynthesizing acarbose and homologous pseudo-oligosaccharides from acarbose-producing microorganisms other than *Streptomyces glaucescens* GLA.O, characterized in that, proceeding from the recombinant DNA molecule according to claim 4, a) PCR primers are prepared,
b) these PCR primers are used for accumulating DNA fragments of gemonic DNA or cDNA from a corresponding microorganism,
c) the accumulated fragments are isolated and characterized, and
d) where appropriate, employed in a process as described in the previous paragraph.

The described processes for isolating a gene cluster for the biosynthesis of acarbose and homologous pseudo-oligosaccharides from acarbose-producing microorganisms other than *Streptomyces glaucescens* GLA.O are characterized in that the microorganisms are selected from the group consisting of Actinomycetales, such as *Streptomyces, Actinoplanes, Ampullariella* and *Streptosporangium strains, Streptomyces hygroscopicus var. limoneus* and *Streptomyces glaucescens*, preferably from the group consisting of *Streptomyces glaucescens* GLA.C) and Actinoplanes sp.

The invention furthermore relates to the use of *Streptomyces glaucescens* GLA.O for isolating acarbose.

The invention will now be explained in more detail with the aid of the examples, tables and figures, without being restricted thereto.

All the plasmid isolations were carried out using a Macherey and Nagel (Düren, Germany) isolation kit (Nucleobond®) in accordance with the manufacturer's instructions. Molecular biological procedures were carried out in accordance with standard protocols (Sambrock et al. (1989) Molecular cloning: A Laboratory Manual, 2nd ed. Cold Spring Harbor Laboratory, USA) or in accordance with the instructions of the respective manufacturer. DNA and protein sequences were examined using Genetics Computer Group Software, Version 8 (proclaims: FastA, TFastA, BlastX, Motifs, GAP and CODONPREFERENCE) and the SwissProt (release 32), EMBL (release 46) and Prosite (release 12.2) databases. The molecular biological manipulation of *Streptomyces glaucescens* and Actinoplanes (DNA isolation and DNA transformations) were carried out as described in Hopwood et al.: Genetic Manipulation of *Streptomyces: A Laboratory Manual. The John Innes Foundation, Norwich, UK*, 1985 and Motamedi and Hutchinson: Cloning and heterologous expression of a gene cluster for the biosynthesis of tetracenomycin C, the anthracycline antitumor antibiotic of *Streptomyces glaucescens*. Proc. Natl. Acad. Sci. USA 84:4445–4449 (1987).

In general, hybridizations were performed using the "Non-radioactive DNA labeling kit" from Boehringer Mannheim (Cat. No. 1175033). The DNA was visualized using the "Luminescent Detection Kit" from Boehringer Mannheim (Cat. No. 1363514). In all the examples given in this patent application, hybridization was carried out under stringent conditions: 68° C., 16 h. 5×SSC, 0.1% N-laurylsarcosine, 0.020/c SDS, 1% Blocking Reagent (Boehringer Mannheim). SSC denotes 0.15M NaCl/0.015M sodium citrate. The definition of "stringent conditions" which is given here applies to all aspects of the present invention which refer to "stringent conditions". In this connection, the manner of achieving this stringency, i.e. the cited hybridization conditions, is not intended to have a limiting effect since the skilled person can select other conditions as well in order to achieve the same stringent conditions, e.g. by means of using other hybridization solutions in combination with other temperatures.

EXAMPLE 1

Synthesis and Sequences of the PCR Primers and Amplification of the Fragments from *S. glaucescens* GLA.O The PCR was carried out under standard conditions using in each case 100 pmol of primer 1 and of primer 2 in 100 $\mu$l of reaction mixture

| | |
|---|---|
| PCR buffer[1] | 10 $\mu$l |
| PCR primers | in each case 2.5 $\mu$l |
| dNTPs | in each case 0.2 mM |
| BSA (10 mg/ml) | 1 $\mu$l |
| Template DNA | 1 $\mu$g (1 $\mu$l) |
| Taq polymerase[2] (5 units/ml) | 1.5 $\mu$l |
| H$_2$O | to make up to 100 $\mu$l |

[1]Promega
[2]Boehringer Mannheim

The samples are overlaid with 75, $\mu$l of mineral oil and the amplification is carried out using a Perkin Elmer TC1 DNA thermal cyler.
Parameters:

| Cycles | Temperature | Duration |
|---|---|---|
| 1 | 96° C. | 5 min |
| | 74° C. | 5 min |
| 30 | 95° C. | 1.5 min |
| | 74° C. | 1.5 min |
| 1 | 74° C. | 5 min |

Table 1 lists the sequences of the degenerate primers which should be used for amplifying dTDP-glucose dehydratases from different streptomycetes.

TABLE 1

Primer sequences for amplifying dTDP-glucose 4,6-dehydratases

| | | |
|---|---|---|
| Primer 1: | CSGGSGSSGCSGGSTTCATSGG | (SEQ ID NO.: 1) |
| Primer 2: | GGGWVCTGGYVSGGSCCGTAGTTG | (SEQ ID NO.: 2) |

In this table, S = G or C, W = A or T, V = A or G, and Y = T or C.

EXAMPLE 2

DNA Sequences of the PCFO Fragments Isolated from *Streptomyces glaucescens* GLA.O The sequencing was performed by the dideoxy chain termination method of Sanger et al. (PNAS USA, 74: 5463–5467 (1977)). The reactions were carried out using the Auto Read Sequenzing Kit® from Pharmacia Biotech (Freiburg, Germany) in accordance with the manufacturer's instructions. An ALF DNA Sequencer® from Pharmacia Biotech (Freiburg, Germany) was used for separation and detection.

The subsequent cloning of the PCR fragments (Sure Clone Kit® Pharmacia Biotech, Frieburg) into the *E. coli* vector pUC 18, and the sequencing of the fragment, provided support for the supposition that the fragment encoded a dTDP-glucose 4,6-dehydratase. However, 2 different genes were isolated which both exhibit high degrees of homology with dTDP-glucose 4,6-dehydratase but are not identical. In that which follows, the PCR fragments are designated acbD* and HstrE*.

The sequences of the isolated PCR fragments are shown in Table 2A and 2B and the homology comparison of the deduced amino acid sequences of HstrE* and acbD* is shown in Table 2C. The two proteins exhibit an identity of only 65%.

TABLE 2A

DNA sequence of acbD (primer-binding sites are underlined, SEQ ID NO.:3)

```
    Primer 1
1   CCCGGGCGGG GCGGGGTTCA TCGGCTCCGC CTACGTCCGC CGGCTCCTGT
51  CGCCCGGGGC CCCCGGCGGC GTCGCGGTGA CCGTCCTCGA CAAACTCACC
101 TACGCCGGCA GCCTCGCCCG CCTGCACGCG GTGCGTGACC ATCCCGGCCT
151 CACCTTCGTC CAGGGCGACG TGTGCGACAC CGCGCTCGTC GACACGCTGG
201 CCGCGCGGCA CGACGACATC GTGCACTTCG CGGCCGAGTC GCACGTCGAC
251 CGCTCCATCA CCGACAGCGG TGCCTTCACC CGCACCAACG TGCTGGGCAC
301 CCAGGTCCTG CTCGACGCCG CGCTCCGCCA CGGTGTGCGC ACCCTCGTGC
351 ACGTCTCCAC CGACGAGGTG TACGGCTCCC TCCCGCACGG GGCCGCCGCG
401 GAGAGCGACC CCCTGCTCCC GACCTCGCCG TACGCGGCGT CGAAGGCGGC
451 CTCGGACCTC ATGGCGCTCG CCCACCACCG CACCCACGGC CTGGACGTCC
501 GGGTGACCCG CTGTTCGAAC AACTACGGCC CGCACCAGTT CCCGGG
                                          Primer 2
```

TABLE 2B

DNA sequence of HstrE (primer-binding sites are underlined, SEQ ID NO.:4)

```
    Primer 2
1   CCCCGGGTGC TGGTAGGGGC CGTAGTTGTT GGAGCAGCGG GTGATGCGCA
51  CGTCCAGGCC GTGGCTGACG TGCATGGCCA GCGCGAGCAG GTCGCCCGAC
101 GCCTTGGAGG TGGCATAGGG GCTGTTGGGG CGCAGCGGCT CGTCCTCCGT
151 CCACGACCCC GTCTCCAGCG AGCCGTAGAC CTCGTCGGTG GACACCTGCA
201 CGAAGGGGGC CACGCCGTGC CGCAGGGCCG CGTCGAGGAG TGTCTGCGTG
251 CCGCCGGCGT TGGTCCGCAC GAACGCGGCG GCATCGAGCA GCGAGCGGTC
301 CACGTGCGAC TCGGCGGCGA GGTGCACGAC CTGGTCCTGG CCGGCCATGA
351 CCCGGTCGAC CAGGTCCGCG TCGCAGATGT CGCCGTGGAC GAAGCGCAGC
401 CGGGGGTGGT CGCGGACCGG GTCGAGGTTG GCGAGGTTGC CGGCGTAGCT
451 CAGGGCGTCG AGCACGGTGA CGACGGCGTC GGGCGGCCCG TCCGGACCGA
501 GGAGGGTGCG GACGTAGTGC GAGCCCATGA ACCCCGCCGC C
                               Primer 1
```

TABLE 2C

Homology comparison of the deduced amino acid sequences of the PCR products HstrE* and acbD* (program: GAP)

| | | | |
|---|---|---|---|
| Quality: | 196.3 | Length: | 182 |
| Ratio: | 1.091 | Gaps: | 0 |
| Percent similarity: | 77.654 | Percent identity: | 65.363 |

PCRstrE.Pep x PCRacbD.Pep

```
            *         *         *         *         *
  1 ..AAGFMGSHYVRTLLGPDGPPDAVVTLDALSYAGNLANLDPVRDHPRL     48
     :||||:||  |||  ||:|..:...|||||  |.|||.||.|.:|||||  |
  1 PGGAGFIGSAYVRRLLSPGAPGGVAVTVLDKLTYAGSLARLHAVRDHPGL     50
```

TABLE 2C-continued

Homology comparison of the deduced amino acid sequences of the PCR products HstrE* and acbD* (program: GAP)

```
           *         *         *         *         *
 49 RFVHGDICDADLVDRVMAGQDQVVHLAAESHVDRSLLDAAAFVRTNAGGT           98
    ||:||:||..||| : | :|::||:||||=||||: |.:||.|||. ||
 51 TFVQGDVCDTALVDTLAARHDDIVHFAAESHVDRSITDSGAFTRTNVLGT          100

*         *         *         *         *
 99 QTLLDAALRHGVAPFVQVSTDEVYGSLETGSWTEDEPLRPNSPYATSKAS          148
    |.|||||||||| .: :|||||||||. |. .|.:|| |.||||.|||.
101 QVLLDAALRHGVRTLVHVSTDEVYGSLPHGAAAESDPLLPTSPYAASKAA          150

*         *         *
149 GDLLALAMHVSHGLDVRITRCSNNYGPYQHPG                            180
    :||:||| | .||||||:||||||||.| |
151 SDLMALAHHRTHGLDVRVTRCSNNYGPHQFP.                            181
``` in each case, upper row: SEQ ID NO.: 5
in each case, lower row: SEQ ID NO.: 6

EXAMPLE 3

Southern Analysis Using Chromosomal DNA from *Streptomyces glaucescens* GLA.O and the Isolated and Labeled PCR Fragments The cells were grown in R2YENG medium and harvested for the DNA isolation after 30 h. The chromosomal DNA was isolated from *S. glaucescens* GLA.O as described in Hopwood et al. (1985) Genetic manipulations of *Streptomyces: a laboratory manual. The John Innes Foundation, Norwich UK).*

A Southern blot analysis was carried out using the *S. glaucescens* GLA.O producer strain chromosomal DNA, which was digested with PstI, BglII and BamHI, using the labeled probes consisting of the acbD* and HstrE* PCR fragments. The two PCR fragments were labeled with digoxygenin in accordance with the manufacturer's (Boehringer Mannheim; Mannheim) instructions, and a digest of the *Streptomyces glaucescens* GLA.O producer strain chromosomal DNA was separated on an agarose gel. The DNA was transferred by capillary transfer to nylon membranes and DNA regions which were homologous with the labeled probes were subsequently visualized following hybridization.

The two genes label different DNA regions (FIG. 1 and FIG. 2), with the fragments which were labeled by HstrE* having to be gene fragments from *Streptomyces glaucescens* GLA.O hydroxystreptomycin biosynthesis. While the DNA sequence is not published, the high degree of homology of the protein sequence deduced from HstrE* with StrE (Pissowotzki et al. (1991) Mol. Gen. Genet. 231: 113–123) from *Streptomyces griseus* N2-3-11 streptomycin biosynthesis (82% identity) and the concordance of the HstrE*-labeled DNA fragments (FIG. 1) with the published restriction map of the *Streptomyces glaucescens* GLA.O hydroxystreptomycin gene cluster (Retzlaff et al. (1993) Industrial Microorcianisms. Basic and applied molecular genetics ASM, Washington D.C., USA) permits this conclusion. The fragments which were labeled by the acbD* probe (FIG. 2) belong to a DNA region which has not previously been investigated. This region encodes the enzymes for biosynthesizing the *Streptomyces glaucescens* GLA.O pseudo-oligosaccharides.

EXAMPLE 4

Cloning the 6.8 kb PstI Fragment

Inter alia, the acbD* PCR fragment labels a 6.8 kB PstI DNA fragment (FIG. 2). This DNA fragment was isolated as follows. The region of the gel was excised with a razor blade and the DNA was isolated from the gel using an isolation kit from Pharmacia Biotech and cloned into plasmid pUC19 which had been cut with the restriction enzyme PstI (plasmid pacbl); this latter plasmid was then transformed into the *E. coli* strain DH5α. The individual clones were subcultured from these plates and a plasmid DNA isolation was carried out using these clones. A PCR amplification using the above-described primers 1 and 2 (Tab. 1) was carried out using the DNA from these clones (250). In this manner, the appropriate *E. coli* clone containing the 6.8 kb PstI fragment was isolated.

EXAMPLE 5

Sequencing the Isolated 6.8 kb PstI DNA Fragment

The DNA was digested with various restriction enzymes and individual DNA fragments were cloned into pUC19. The DNA sequence of the entire fragment, which is shown in Tab. 4 (SEQ ID NO.:7), was then determined. The DNA sequence of the 6.8 kb PstI fragment was only partially confirmed by supplementary sequencing of the opposing strand. Several open reading frames, encoding various proteins, were found (programs: CODONPREFERENCE and BlastX). A total of 6 coding regions was found, i.e. a gene having a high degree of homology with ATP-binding protein, acbA, an aminotransferase acbB, a dTDP-glucose synthase acbC, a dTDP-glucose dehydratase acbD, a regulatory gene having homologies with the Lacd protein family acbE, and a protein having similarities to sugar-binding proteins acbF. The sequences of the acbA and acbF genes were only determined in part. The homologies with other proteins from the databases, and the properties of the putative proteins, are summarized in Tab. 3. FIG. 3 shows, in summary form, a restriction map of the fragment, containing the most important restriction cleavage sites mentioned in the text, and the arrangement of the identified open reading frames.

TABLE 3

Analysis of the identified open reading frames on the 6.8 kb
PstI fragment from *Streptomyces glaucescens* GLA.O

| ORF | Amino acid | MW | FastA[§] | % Identity | Accession number[§] |
|---|---|---|---|---|---|
| acbA | 239 | * | MalK *E coli* | 29% | P02914 |
| acbB | 429 | 45618 | DgdA, *Burkholderia cepacia* | 32% | P16932 |
| acbC | 355 | 37552 | StrD, *Streptomyces griseus* | 60% | P08075 |
| acbD | 325 | 35341 | StrE, *Streptomyces griseus* | 62% | P29782 |
| acbE | 345 | 36549 | DegA, *Bacillus. subtilis* | 31% | P37947 |
| acbF | 396 | * | MalE, *E. coli* | 22% | P02928 |

*incomplete open reading frame;
[§]Swiss-Prot database (release 32)

EXAMPLE 6

Deletion of Genes acbBCD for Pseudo-oligosaccharide Biosynthesis from the *Streptomyces glaucescens* GLA.O Chromosome Evidence that the identified DNA fragment encoded pseudo-oligosaccharide biosynthesis genes was produced as follows. A 3.4 kb gene region (EcoR1/SstI fragment b, FIG. 3) was replaced with the erythromycin resistance gene (1.6 kb) and cloned, together with flanking DNA regions from the 6.8 kb PstI fragment (pacb1) into the temperature-sensitive plasmid pGM160. The plasmid was constructed as described in the following: the 2.2 kb EcoR1/HindIII fragment (c, FIG. 3) from plasmid pacb1 was cloned into pGEM7zf (Promega, Madison, Wis., USA; plasmid pacb2), and the 1 kb SstI fragment from pacb1 (a, FIG. 3) was cloned into pUC19 (plasmid pacb3). A ligation was then carried out using the following fragments. The plasmid pGM160 (Muth et al. (1989) Mol. Gen Genet. 219:341–348) was cut with BamH/HindIII, the plasmid pacb2 was cut with XbaI/BamHI (c, FIG. 3), the plasmid pacb3 was cut with EcoRI/HindIII (a, FIG. 3), and the plasmid pIJ4026 (Bibb et al. (1985) Gene 38:215–226) was cut with EcoRI/XbaI in order to isolate the 1.6 kb ermE resistance gene.

The fragments were ligated in a mixture and transformed into *E. coli* DH5α and selected on ampicillin. The resulting plasmid, i.e. pacb4, was isolated from *E. coli* DH5α, tested for its correctness by means of restriction digestion and then transferred by protoplast transformation into *S. glaucescens* GLA.O. The transformants were selected with thiostrepton at 27° C. in R2YENG agar. The transformants were subsequently incubated at the non-permissive temperature of 39° C. and integration of the plasmid into the genome by way of homologous recombination thereby instituted (selection with thiostrepton (25 μg/ml) and erythromycin (50 μg/ml)). Under these conditions, the only clones which can grow are those in which the plasmid has become integrated into the genome. The corresponding clones were isolated, caused to sporulate (medium 1, see below) and plated out on erythromycin-containing agar (medium 1). Individual clones were isolated once again from this plate and streaked out on both thiostrepton-containing medium and erythromycin-containing medium. The clones which were erythromycin-resistant but no longer thiostrepton-resistant were analyzed. In these clones, the acbBCD genes had been replaced with ermE. Several clones were examined and the strain *S. glaucescens* GLA.O Aacb was finally selected as the reference strain (erythromycin-resistant, thiostrepton-sensitive) for further investigation.

Medium 1

| Yeast extract | 4 g/L |
|---|---|
| Malt extract | 10 g/L |
| Glucose | 4 g/L |
| Agar | 15 g/L |
| pH | 7.2 |

A further experiment examined whether the corresponding strain still produced acarbose. Some clones were grown and investigated for formation of the α-amylase inhibitor in a bioassay; however, no activity was found. The mutants were subsequently further characterized by means of Southern hybridization. Integration of the ermE gene had taken place at the predicted site. FIG. 4 shows a Southern hybridization which was carried out with the wild type and with the *Streptomyces glaucescens* GLA.O Aacb deletion mutant. The SstI fragment from pacb3 was used as the probe. The chromosomal DNA was isolated from the wild type and mutant and digested with the enzymes PstI and PstI/HindIII. The fragment pattern obtained for the deletion mutant corresponds to the predicted recombination event. The wild type exhibits the unchanged 6.8 kb PstI fragment, whereas the mutant exhibits a fragment which has been truncated by 1.8 kb (compare lanes 1 and 3, FIG. 4). Integration of the ermE resistance gene additionally introduced an internal HindIII cleavage site into the PstI fragment (compare lanes 2 and 4, FIG. 4).

EXAMPLE 7

Inhibition of α-amylase by Acarbose

Using an enzymic test for detecting starch (TC-Starch, Boehringer-Mannheim, Cat. No. 297748), it was possible to demonstrate that the compound isolated from *Streptomyces claucescens* GLA.O inhibits α-amylase. Test principle: starch is cleaved into D-glucose by amyloglucosidase. The glucose is then converted with hexokinase into glucose-6-phosphate and the latter is converged with glucose-6-phosphate dehydrogenase into D-gluconate-6-phoshaite. This reaction produces NADPH, whose formation can be determined photometrically. Acarbose inhibits the (α-amylase and thereby prevents the formation of D-glucose and ultimately the formation of NADPH as well.

EXAMPLE 8

Medium for Growing *S. glaucescens* GLA.O and Producing Acarbose

The fermentation was carried out, at 27° C. on an orbital shaker at 120 rpm, in 500 ml Erlenmeyer flasks which were fitted with side baffles and which contained 100 ml of medium 2. The fermentation was terminated after 2 or 3 days. The pseudo-oligosaccharides were detected in a plate diffusion test as described in Example 9. No (α-amylase inhibitors were produced when medium 3 was used. This means that the production of the pseudo-oligosaccharides is inhibited by glucose. Other sugars, such as maltose and sucrose, or complex sugar sources (malt extract) can also come into consideration for producing pseudo-oligosaccharides using *S. glaucescens* GLA.O.

Medium 2:

| | | |
|---|---|---|
| Soybean flour | 20 g/L | |
| Starch | 20 g/L | |
| pH | 7.2 | |

Medium 3:

| | | |
|---|---|---|
| Soybean flour | 20 g/L | |
| Glucose | 20 g/L | |
| pH | 7.2 | |

EXAMPLE 9

Biotest Using Mucor Miehei

A suspension of spores of the strain Mucor miehei was poured into agar (medium 5) ($10^5$ spores/ml), and 10 ml of this mixture were in each case poured into Petri dishes. Paper test disks ((6 mm diameter) were loaded with 10 μl of acarbose [lacuna] (1 mg/ml) or with a sample from an S. glaucescens culture and laid on the test plates. The plates were then incubated at 37° C. Inhibition halos appeared on the starch-containing medium 5. A plate which was prepared with glucose (medium 4) instead of starch was used as a control. On this medium, no inhibition halo formed around the filter disks loaded with active compound.

Media 4 and 5:

| | | |
|---|---|---|
| $KH_2PO_4 \times 3H_2O$ | 0.5 g | |
| $MgSO_4 \times 7H_2O$ | 0.2 g | |
| NaCl | 0.1 g | |
| Ammonium sulfate | 5 g | |
| Yeast nitrogen base | 1.7 g | |
| Glucose (4) or starch (5) | 5 g | |
| Agar | 15 g | |

EXAMPLE 10

Transformation of S. glaucescens GLA.O

Protoplasts of the Streptomyces glaucescens strain were isolated as described in Motamedi and Hutchinson ((1987) PNAS USA 84: 4445–4449), and the isolated plasmid DNA was transferred into the cells by means of PEG transformation as explained in Hopwood et al. ((1985) Genetic manipulations of Streptomyces: a laboratory manual. The John Innes Foundation, Norwich UK). The protoplasts were regenerated on R2YENG medium at 30° C. (Motamedi and Hutchinson (1987) PNAS USA 84: 4445–4449). After 18 h, the agar plates were overlaid with a thiostrepton-containing solution and incubated at 30° C. (final concentration of thiostrepton: 20 μg/ml).

EXAMPLE 11

Isolation of the Pseudo-oligosaccharides from Streptomyces glaucescens GLA.O, HPLC Analysis and Mass Spectroscopy Isolation The culture broth was separated from the mycelium by filtration. The culture filtrate which has been obtained in this way is then loaded onto an XAD16 column, after which the column is washed with water and the active components are eluted with 30% methanol. The eluate was concentrated down to the aqueous phase and the latter was extracted with ethyl acetate in order to remove lipophilic impurities. The aqueous phase was then concentrated and the active components were further purified in 5% methanol using a biogel P2 column. The individual fractions are collected in a fraction collector. The individual fractions were analyzed by means of the Mucor miehei biotest. Active eluates were rechromatographed, for further purification, in 5% methanol on biogel P2. The material which was isolated in this way was investigated by HPLC and MS.

HPLC

Column: Nucleosil® 100 C-18

Eluent 0.1% phosphoric acid=A/acetonitrile=B

Gradient: from 0 to 100% B in 15 min

Detection: 215 nm

Flow 2 ml/min

Injection volume: 10–20 μl

Using HPLC, it was not possible to distinguish the pseudo-oligosaccharide preparation from S. glaucescens GLA.O from authentic acarbose. Both the retention time and the UV absorption spectrum of the two components were identical in this eluent system. The pseudo-oligosaccharide mixture was not fractionated under these conditions.

Mass Spectroscopic Analysis (MS)

The molecular weights and the fragmentation pattern of authentic acarbose and the pseudo-oligosaccharides isolated from Streptomyces glaucescens GLA.O were determined by means of elecltrospray MS. Analysis of the acarbose which is commercially obtainable from Bayer (Glucobay) gave a mass peak at 645.5 (acarbose). The purified samples from S. glaucescens GLA.O contain a mixture of different pseudo-oligosaccharides whose sugar side chains are of different lengths: 969 (acarbose+2 glucose units), 807 (acarbose+1 glucose unit), 645 (corresponds to authentic acarbose). When acarbose and the compound which is isolated from S. glaucescens GLA.O and which has a molecular weight of 645 are fragmented, the same molecular fragments are formed, i.e.: 145 (4-amino-4,6-deoxyglucose), 303 (Acarviosin) and 465 (303 together with one glucose unit).

Actinoplanes sp. SE50 also produces a mixture of acarbose molecules having sugar side chains of different length (Truscheit (1984) VIIIth International Symposium on Medicinal Chemistry, Proc. Vol 1. Swedish Academy of Pharmaceutical Sciences, Stockholm, Sweden). The length of the sugar side chains can be influenced by the choice of the fermentation parameters and of the substrate in the nutrient solution.

EXAMPLE 12

Southern Hybridization Using Actinoplanes sp. SE50/110 (ATCC31044)

The chromosomal DNA was isolated from the strain Actinoplanes sp. SE50/100 and digested with restriction enzymes (PstI and BamHI). A Southern hybridization was then carried out using a probe which encompasses the coding region of the dTDP-glucose 4,6-dehydratase acbD from Streptomyces glaucescens GLA.O (fragment d, FIG. 3). The probe hybridizes with distinct bands from Actinoplanes sp. SE50/110 (FIG. 5, lanes 1 and 2). This provides the possibility of isolating the corresponding fragments from Actinoplanes sp. SE50/100 and other strain lines. Whether these DNA regions are in fact, involved in the biosynthesis of acarbose remains to be demonstrated in subsequent investigations. Alternatively, the PCR primers 1 and 2 (Tab. 1) could also be used for amplifying the dTDP-glucose 4,6-dehydratase from Actinoplanes sp.

Legends:

FIG. 1: Southern hybridization using *S. glaucescens* GLA.O. Lane 1: PstI, lane 2: BamHI, lane 3: BglII. The labeled PCR fragment HstrE* was used as the probe. Labeling of DNA fragments which are involved in the biosynthesis of hydroxy-streptomycin.

FIG. 2: Southern hybridization using *S. glaucescens* GLA.O. Lane 1: PstI, lane 2: BamHI, lane 3: BglII. The labeled PCR fragment acbD* was used as the probe. Labeling of DNA fragments which are involved in the biosynthesis of the pseudo-oligosaccharides.

FIG. 3: Restriction map of the 6.83 kb PstI fragment from *Streptomyces glaucescens* GLA.O. Open reading frames and the direction in which each is transcribed are indicated by arrows. The fragments a, b, c and d identify DNA regions which are explained in more detail in the text.

FIG. 4: Southern hybridization using *Streptomyces glaucescens* Δacb: lane 1: PstI, lane 2: PstI/HindIII, and *Streptomyces glaucescens* GLA.O lane 3: PstI, lane 4: PstI/HindIII. The labeled 1.0 kb SstI fragment a (FIG. 3) was used as the probe.

FIG. 5: Southern hybridization using Actinoplanes sp. SE50/100: lane 1: PstI, lane 2: BamHI and *Streptomyces glaucescens* GLA.O lane 3: PstI. The labeled 1.0 kb SmaI/EcoRI fragment d (dTDP-glucose 4,6-hydratase, FIG. 3) was used as the probe. The arrows indicate the labeled DNA fragments (BamHI: 2.1 and 0.7 kb, PstI: ~11–12 kb)

Tab. 4: DNA sequence of the 6.8 kb PstI fragment from *Streptomyces glaucescens* GLA.O (SEQ ID NO.: 7). The deduced amino acid sequences, (SEQ ID NO.: 8–13) of the identified open reading frames are given under the DNA sequences. Start and stop codons and potential ribosome binding sites are underlined.

acbA: SEQ ID NO.: 8
acbB: SEQ ID NO.: 9
acbC: SEQ ID NO.: 10
acbD: SEQ ID NO.: 11
acbE: SEQ ID NO.: 12
acbF: SEQ ID NO.: 13

TABLE 4

(SEQ ID NO.: 7, 8, 9, 10, 11, 12, 13)

```
        p
        s
        t
        I
CTGCAGGGTTCCCTGGTGCACGACCCGCCCCTGGTCGACGACCAGGGCGCTGTCGCAGAT
---------+---------+---------+---------+---------+---------+   60
GACGTCCCAAGGGACCACGTGCTGGGCGGGACCAGCTGCTGGTCCCGCGACAGCGTCTA
  Q  L  T  G  Q  H  V  V  R  G  Q  D  V  V  L  A  S  D  C  I -

CGCGGCGATGTCGGCGATGTCGTGGCTGGTGAGCACCACGGTGGTGCCCAGTTCCCGGTG
---------+---------+---------+---------+---------+---------+  120
GCGCCGCTACAGCCGCTACAGCACCGACCACTCGTGGTGCCACCACGGGTCAAGGGCCAC
  A  A  I  D  A  I  D  H  S  T  L  V  V  T  T  G  L  E  R  H -

GGCGCGGTTGACCAGCCGGCGCACCGCGTCCTTCAGCACCATGTCGAGGCCGATCGTGGG
---------+---------+---------+---------+---------+---------+  180
CCGCGCCAACTGGTCGGCCGCGTGGCGCAGGAAGTCGTGGTACAGCTCCGGCTAGCACCC
  A  R  N  V  L  R  R  V  A  D  K  L  V  M  D  L  G  I  T  P -

CTCGTCCCAGAACAGCACGGCCGGGTCGTGCAGCAGGCTCGCCGCGATCTCGGCGCGCAT
---------+---------+---------+---------+---------+---------+  240
GAGCAGGGTCTTGTCGTGCCGGCCCAGCACGTCGTCCGAGCGGCGCTAGAGCCGCGCGTA
  E  D  W  F  L  V  A  P  D  H  L  L  S  A  A  I  E  A  R  M - s
        p
        h
        I
GCGCTGTCCGAGGCTGAGCTGCCGCACGGGGTGGACCCCAGCGCGTCGATGTCGAGGAG
---------+---------+---------+---------+---------+---------+  300
CGCGACAGGCTCCGACTCGACGGCGTGCCCCCACCTGGGGTCGCGCAGCTACAGCTCCTC
  R  Q  G  L  S  L  Q  R  V  P  T  S  G  L  A  D  I  D  L  L -

GTCCCGGAACAGGGCGAGGTTGCGCCGGTAGACCGGTCCGGGGATGTCGTAGATGCGGCG
---------+---------+---------+---------+---------+---------+  360
CAGGGCCTTGTCCCGCTCCAACGCGGCCATCTGGCCAGGCCCCTACAGCATCTACGCCGC
  D  R  F  L  A  L  N  R  R  Y  V  P  G  P  I  D  Y  Z  R  R -

K
           p
           n
           I
CAGGATGCGGAAGGAGTCGGGTACCGACAGGTCCCACCAGAGCTGGCTGCGCTGGCCGAA
---------+---------+---------+---------+---------+---------+  420
GTCCTACGCCTTCCTCAGCCCATGGCTGTCCAGGGTGGTCTCGACCGACGCGACCGGCTT
  L  I  R  F  S  D  P  V  S  L  D  W  W  L  Q  S  R  Q  G  F -
```

TABLE 4-continued (SEQ ID NO.: 7, 8, 9, 10, 11, 12, 13)

```
GACGACGCCGATCGTCGCGGGCGTTGCGCTGCCGGTGCCGGTAGGGCTCCAGCCCGGCGAC
---------+---------+---------+---------+---------+---------+    480
CTGCTGCGGCTAGCACGCCCGCAACGCGACGGCCACGGCCATCCCCAGGTCGGGCCGCTG
  V  V  G  I  T  R  A  N  R  Q  R  H  R  Y  P  E  L  G  A  V  -

CGTGCAGCGGCCGGAGGTGGGGGTCATGATGCCGGTCAGCATCTTGATCGTGGTCGACTT
---------+---------+---------+---------+---------+---------+    540
GCACGTCGCCGGCCTCCACCCCAGTACTACGGCCAGTCGTAGAACTAGCACCAGCTGAA
  T  C  R  G  S  T  P  T  M  I  G  T  L  M  K  I  T  T  S  K  -

GCCGGCTCCGTTGGCGCCGATGTAGGCGGTCTTCGTGCCGGCCGGTATCTCGAAGGAGAC
---------+---------+---------+---------+---------+---------+    600
CGGCCGAGGCAACCGCGGCTACATCCGCCAGAAGCACGGCCGGCCATAGAGCTTCCTCTG
  G  A  G  N  A  G  I  Y  A  T  K  T  G  A  P  I  E  F  S  V  -
                                                        K
                                                        p
                                                        n
                                                        I
GTCGTCGACGGCGCGCACGACGCGGTACCGGCGGGTCAGGAGGGTGGAGAGGCTGCCGAG
---------+---------+---------+---------+---------+---------+    660
CAGCAGCTGCCGCGCGTGCTGCGCCATGGCCGCCCAGTCCTCCCACCTCTCCGACGGCTC
  D  V  A  R  V  V  R  Y  R  R  T  L  L  T  S  L  S  G  L     -

CAGGCCGGGCTCGCGTTCGGCCAGCCGGAACTCCTTGAGGAGGTGTTCGGCCACGATCAC
---------+---------+---------+---------+---------+---------+
GTCCGGCCCGAGCGCAAGCCGGTCGGCCTTGAGGAACTCCTCCACAAGCCGGTGCTAGTG
                                                           *   -
  L  G  P  E  R  E  A  L  R  F  E  K  V  L  H  E  A  V  I  V  -
                                                        ──── acbA
GCGATCACCCGCTCGACGGCCGTCTCCAGCAGGCGCAGGCCCTCGTCGAGCAGCGCCTCG
---------+---------+---------+---------+---------+---------+    780
CGCTAGTGGGCGAGCTGCCGGCAGAGGTCGTCCGCGTCCGGGAGCAGCTCGTCGCGGAGC
  A  I  V  R  E  V  A  T  E  L  L  R  L  G  E  D  L  L  A  E  -

TCGAGGGTGAACGGCGGTGCCAGCCGCAGGATGTGGCCGCCCAGGGAGGTGCGCAGCCCC
---------+---------+---------+---------+---------+---------+    840
AGCTCCCACTTGCCGCCACGGTCGGCGTCCTACACCGGCGGGTCCCTCCACGCGTCGGGG
  D  L  T  F  P  P  A  L  R  L  I  H  G  G  L  S  T  R  L  G  -
                              s
                              m
                              a
                              I
AGGTCGAGGGCGGTGGTGTAGACGGCCCGGGCGGTCTCGGGGGCGGGTGCCCGGCCGACG
---------+---------+---------+---------+---------+---------+    900
TCCAGCTCCCGCCACCACATCTGCCGGGCCCGCCAGAGCCCCCGCCCACGGGCCGGCTGC
  L  D  L  A  T  T  Y  V  A  R  A  T  E  P  A  P  A  R  G  V  -

GCGTCGGTGACGAACTCCAGGCCCCACAGCAGTCCGAGGCCGCGTACCTGGCCGAGCTGG
---------+---------+---------+---------+---------+---------+    960
CGCAGCCACTGCTTGAGGTCCGGGGTGTCGTCAGGCTCCGGCGCATGGACCGGCTCGACC
  A  D  T  V  F  E  L  G  W  L  L  G  L  G  R  V  Q  G  L  Q  -
                                          s
                                          s
                                          t
                                          I
GGGAAGCGGGACTCCAGGGCGCGCAGCCGCTCCTGGATGAGCTCGCCGAGGACGCGCACG
---------+---------+---------+---------+---------+---------+   1020
CCCTTCGCCCTGAGGTCCCGCGCGTCGGCGAGGACCTACTCGAGCGGCTCCTGCGCGTGC
  P  F  R  S  E  L  A  R  L  R  E  Q  I  L  E  G  L  V  R  V  -

CGGTCGATCAGCCGGTCGCGCTCGACGACCTCCAGCGTGGCGCGGGCGGCGGCGATCCCC
---------+---------+---------+---------+---------+---------+   1080
GCCAGCTAGTCGGCCAGCGCGAGCTGCTGGAGGTCGCACCGCGCCCGCCGCCGCTAGGGG
  R  D  I  L  R  D  R  E  V  V  E  L  T  A  R  A  A  A  I  G  -
                              s
                              m
                              a
                              I
AGTGGGTTGCTCGCGTACGTCGAGGCGTACGCCCCGGGGTGGCCGCCTCCGGCCTGCGCA
---------+---------+---------+---------+---------+---------+   1140
TCACCCAACGAGCGCATGCAGCTCCGCATGCGGGCCCCACCGGCGGAGGCCGGACGCGT
  L  P  N  S  A  Y  T  S  A  Y  A  G  P  H  G  G  G  A  Q  A  -
```

TABLE 4-continued (SEQ ID NO.: 7, 8, 9, 10, 11, 12, 13)

```
GCTTCCGCGCGTCCGGCCAGCACGGCGAAGGGGAATCCGCTCGCGGTGCCCTTGGACAGC
---------+---------+---------+---------+---------+---------+   1200
CGAAGGCGCGCAGGCCGGTCGTGCCGCTTCCCCTTAGGCGAGCGCCACGGGAACCTGTCG
 A  E  A  R  G  A  L  V  A  F  P  F  G  S  A  T  G  K  S  L   -

ATCGCCAGGTCCGGCTCGATGCCGAACAGTTCGCTGGCGAGGAAGGCGCCGGTGCGCCCG
---------+---------+---------+---------+---------+---------+   1260
TAGCGGTCCAGGCCGAGCTACGGCTTGTCAAGCGACCGCTCCTTCCGCGGCCACGCGGGC
 M  A  L  D  P  E  I  G  F  L  E  S  A  L  F  A  G  T  R  G   -

CCGCCGGTGAGGACCTCGTCGGCGACGAGCAGCACGCCGCCGTCCCGGCAGGCGCCGGCG
---------+---------+---------+---------+---------+---------+   1320
GGCGGCCACTCCTGGAGCAGCCGCTGCTCGTCGTGCGGCGGCAGGGCCGTCCGCGGCCGC
 G  G  T  L  V  E  D  A  V  L  L  V  G  G  D  R  C  A  G  A   -

ATCCGCTCCCAGTAGCCGGGGGGCGGCACGATGACGCCTGCCGCGCCGAGGACGGGTTCG
---------+---------+---------+---------+---------+---------+   1380
TAGGCGAGGGTCATCGGCCCCCCGCCGTGCTACTGCGGACGGCGCGGCTCCTGCCCAAGC
 I  R  E  W  Y  G  P  P  P  V  I  V  G  A  A  G  L  V  P  E   -

AAGACCAGGGCCGAGACGTTGGGCTTCTCCGCGATGTGCCGGCGCACGAGGGTCGCGCAC
---------+---------+---------+---------+---------+---------+   1440
TTCTGGTCCCGGCTCTGCAACCCGAAGAGGCGCTACACGGCCGCGTGCTCCCAGCGCGTG
 F  V  L  A  S  V  N  P  K  E  A  I  H  R  R  V  L  T  A  C   -

CGCACGTCGCACGAGGGGTACTCCAGGCCCAGGGGACAGCGGTAGCCAGTAGGGGCTGTA
---------+---------+---------+---------+---------+---------+   1500
GCGTGCAGCGTGCTCCCCATGAGGTCCGGGTCCCTGTCGCCATCGGTCATCCCCGACAT
 R  V  D  C  S  P  Y  E  L  G  L  P  C  R  Y  G  T  P  A  T   -

GCCAGCACGCTGTTGCCGCTGGAGGCCTGGTGGCCGATGTCCCAGTGGACCAGCATCCGG
---------+---------+---------+---------+---------+---------+   1560
CGGTCGTGCGACAACGGCGACTTCCGGACCACCGGCTACAGGGTCACCTGGTCGTAGGCC
 A  L  V  S  N  G  S  F  A  Q  H  G  I  D  W  H  V  L  M  R   -

GCGCCCATGGTCTTGCCGTGGAAGCCGTGGCGCAGGGCGCAGATCCGGTTGCGGCCCGGC
---------+---------+---------+---------+---------+---------+   1620
CGCGGGTACCAGAACGGCACCTTCGGCACCGCGTCCCGCGTCTAGGCCAACGCCGGGCCG
 A  G  M  T  K  G  H  F  G  H  R  L  A  C  I  R  N  R  G  P   -

GCGGCGGTCGCCTGGACGACCCGCAGGGCGGCCTCCACCACCTCCGCGCCGGTGGAGAAG
---------+---------+---------+---------+---------+---------+   1680
CGCCGCCAGCGGACCTGCTGGGCGTCCCGCCGGAGCTGGTGGAGGCGCGGCCACCTCTTC
 A  A  T  A  Q  V  V  R  L  A  A  E  V  V  E  A  G  T  S  F   -

AAGGCGTAGGTGTCGAGCTGTTCGGGCAGCAGCCTGGCGAGCAGTTCCAGCAGGCCGGCG
---------+---------+---------+---------+---------+---------+   1740
TTCCGCATCCACAGCTCGACAAGCCCGTCGTCGGACCGCTCGTCAAGGTCGTCCGGCCGC
 F  A  Y  T  D  L  Q  E  P  L  L  R  A  L  L  E  L  L  G  A   -

CGGTCCGGCGTGGCGCTGTCGTGGACGTTCCACAGGCGGCGGGCCTGGGTGGTGAGTGCC
---------+---------+---------+---------+---------+---------+   1800
GCCAGGCCGCACCGCGACAGCACCTGCAAGGTGTCCGCCGCCCGGACCCACCACTCACGG
 R  D  P  T  A  S  D  H  V  N  W  L  R  R  A  Q  T  T  L  A   -

TCGACGACCTCCGGGTGCCCGTGGCCCAGTGACTGGGTGAGGGTCCCGGCCGCGAAGTCG
---------+---------+---------+---------+---------+---------+   1860
AGCTGCTGGAGGCCCACGGGCACCGGGTCACTGACCCACTCCCAGGGCCGGCGCTTCAGC
 E  V  V  E  P  H  G  H  G  L  S  Q  T  L  T  G  A  A  F  D   -

AGGTACTGGTTGCCGTCCAGGTCGGTCAGAACGGGACCGCGTCCCTCGGCGAAGACCCGG
---------+---------+---------+---------+---------+---------+   1920
TCCATGACCAACGGCAGGTCCAGCCAGTCTTGCCCTGGCGCAGGGAGCCGCTTCTGGGCC
 L  Y  Q  N  G  D  L  D  T  L  V  P  G  R  E  A  F  V  R    -

CGTCCGTGGACGGCTTCCTCGGAGGCGCCCGGCGCCAGGTGGCGGGCCTCCCGTGCCAGG
---------+---------+---------+---------+---------+---------+   1980
GCAGGCACCTGCCGAAGGAGCCTCCGCGGGCCGCGGTCCACCGCCCGGAGGGCACGGTCC
 R  G  H  V  A  E  E  S  A  G  P  A  L  H  R  A  E  R  A  L   -

TGCTGTGTCTGCCGTAAGCCTGTCATCGCTGCCTCTGCTCGTCGGACCGGCTGACGCGAT
---------+---------+---------+---------+---------+---------+   2040
ACGACACAGACGGCATTCGGACAGTAGCGACGGAGACGAGCAGCCTGGCCGACTGCGCTA
 H  Q  T  Q  R  L  G  T  M
```

TABLE 4-continued (SEQ ID NO.: 7, 8, 9, 10, 11, 12, 13)

```
                                    ———— acbB
CGCCGGCGAACTGCGTTGTGGCGCACCACGGTTGGGGCGGCTCGGCGCTGAGTCAAACAC
---------+---------+---------+---------+---------+---------+    2100
GCGGCCGCTTGACGCAACACCGCGTGGTGCCAACCCCGCCGAGCCGCGACTCAGTTTGTG TTGAACACACACCGCTGCAAGAGTTTGCGGGTTCTTTCAGAAAGTTGTTCCGAGCGGCCC
---------+---------+---------+---------+---------+---------+    2160
AACTTGTGTGTGGCGACGTTCTCAAACGCCCAACAAAGTCTTTCAACAACGCTCGCCGGG CGGCACTCTGGTTGAGTCGACCTCCTTACGGCCCCACCACCCCTCACCTTCGAGGAGGGA
---------+---------+---------+---------+---------+---------+    2220
GCCGTGAGACCAACTCAGCTGCACGAATGCCGCGGTGGTGCGCAGTGCAAGCTCCTCCCT CCTGTGAGAACAAGCCCGCAGACCGACCCGCTCCCGCGGAGGCCGAGGTGAAGGCCCTGG
---------+---------+---------+---------+---------+---------+    2280
GGACACTCTTGTTCGGGCGTCTGGCTGGGCGAGGGCGCCTCCGGCTCCACTTCCGGGACC
                                          V   K   A   L   V  -
                                          acbC ————
                                                              P
                                                              v
                                                              u
                                                              I
                                                              I
TCCTGGCAGGTGGAACCGGCAGCAGACTGAGGCCGTTCACCCACACCGCCGCCAAGCAGC
---------+---------+---------+---------+---------+---------+    2340
AGGACCGTCCACCTTGGCCGTCGTCTGACTCCGGCAAGTGGGTGTGGCGGCGGTTCGTCG
   L   A   G   G   T   G   S   R   L   R   P   F   T   H   T   A   A   K   Q   L  -

TGCTCCCCATCGCCAACAAGCCCGTGCTCTTCTACGCGCTGGAGTCCCTCGCCGCGGCGG
---------+---------+---------+---------+---------+---------+    2400
ACGAGGGGTAGCGGTTGTTCGGGCACGAGAAGATGCGCGACCTCAGGGAGCGGCGCCGCC
   L   P   I   A   N   K   P   V   L   F   Y   A   L   E   S   L   A   A   A   G  -

GTGTCCGGGAGGCCGGCGTCGTCGTGGGCGCGTACGGCCGGGAGATCCGCGAACTCACCG
---------+---------+---------+---------+---------+---------+    2460
CACAGGCCCTCCGGCCGCAGCAGCACCCGCGCATGCCGGCCCTCTAGGCGCTTGAGTGGC
   V   R   E   A   G   V   V   V   G   A   Y   G   R   E   I   R   E   L   T   G  -

GCGACGGCACCGCGTTCGGGTTACGCATCACCTACCTCCACCAGCCCCGCCCGCTCGGTC
---------+---------+---------+---------+---------+---------+    2520
CGCTGCCGTGGCGCAAGCCCAATGCGTAGTGGATGGAGGTGGTCGGGGCGGGCGAGCCAG
    D   G   T   A   F   G   L   R   I   T   Y   L   H   Q   P   R   P   L   G   L  -
TCGCGCACGCGGTGCGCATCGCCCGCGGCTTCCTGGGCGACGACGACTTCCTGCTCTACC
---------+---------+---------+---------+---------+---------+    2580
AGCGCGTGCGCCACGCGTAGCGGGCGCCGAAGGACCCGCTGCTGCTGAAGGACGACATGG
    A   H   A   V   R   I   A   R   G   F   L   G   D   D   D   F   L   L   Y   L  -

TGGGGGACAACTACCTGCCCCAGGGCGTCACCGACTTCGCCCGCCAATCGGCCGCCGATC
---------+---------+---------+---------+---------+---------+    2640
ACCCCCTGTTGATGGACGGGGTCCCGCAGTGGCTGAAGCGGGCGGTTAGCCGGCGGCTAG
    G   D   N   Y   L   P   Q   G   C   T   D   F   A   R   Q   S   A   A   D   P  -

CCGCGGCGGCCCGGCTGCTGCTCACCCCGGTCGCGGACCCGTCCGCCTTCGGCGTCGCGG
---------+---------+---------+---------+---------+---------+    2700
GGCGCCGCCGGGCCGACGACGAGTGGGGCCAGCGCCTGGGCAGGCGGAAGCCGCAGCGCC
    A   A   A   R   L   L   L   T   P   V   A   D   P   S   A   F   G   V   A   E  -

AGGTCGACGCGGACGGGAACGTGCTGCGCTTGGAGGAGAAACCCGACGTCCCGCGCAGCT
---------+---------+---------+---------+---------+---------+    2760
TCCAGCTGCGCCTGCCCTTGCACGACGCGAACCTCCTCTTTGGGCTGCAGGGCGCGTCGA
    V   D   A   D   G   N   V   L   R   L   E   E   K   P   D   V   P   R   S   S  -

CGCTCGCGCTCATCGGCGTGTACGCCTTCAGCCCGGCCGTCCACGAGGCGGTACGGGCCA
---------+---------+---------+---------+---------+---------+    2820
GCGAGCGCGAGTAGCCGCACATGCGGAAGTCGGGCCGGCAGGTGCTCCGCCATGCCCGGT
    L   A   L   I   G   V   Y   A   F   S   P   A   V   H   E   A   V   R   A   I  -

TCACCCCCTCCGCCCGCGGCGACCTGGAGATCACCCACGCCGTGCACTGGATGATCGACC
---------+---------+---------+---------+---------+---------+    2880
AGTGGGGAGGCGGGCGCCGCTCGACCTCTAGTGGGTGCGGCACGTCACCTACTAGCTGG
    T   P   S   A   R   G   E   L   E   I   T   H   A   V   Q   W   M   I   D   R  -

GGGGCCTGCGCGTACGGGCCGAGACCACCACCCGGCCCTGGCGCGACACCGGCAGCGCGG
---------+---------+---------+---------+---------+---------+    2940
CCCCGGACGCGCATGCCCGGCTCTGGTGGTGGGCCGGGACCGCGCTGTGGCCGTCGCGCC
    G   L   R   V   R   A   E   T   T   T   R   F   W   R   D   T   G   S   A   E  -
```

TABLE 4-continued (SEQ ID NO.: 7, 8, 9, 10, 11, 12, 13)

```
AGGACATGCTGGAGGTCAACCGTCACGTCCTGGACGGACTGGAGGGCCGCATCGAGGGGA
---------+---------+---------+---------+---------+---------+   3000
TCCTGTACGACCTCCAGTTGGCAGTGCAGGACCTGCCTGACCTCCCGGCGTAGCTCCCCT
  D   M   L   E   V   N   R   H   V   L   D   G   L   E   G   R   I   E   G   K   -

AGGTCGACGCGCACAGCACGCTGGTCGGCCGGGTCCGGGTGGCCGAAGGCGCGATCGTGC
---------+---------+---------+---------+---------+---------+   3060
TCCAGCTGCGCGTGTCGTGCGACCAGCCGGCCCAGGCCCACCGGCTTCCGCGCTAGCACG
  V   D   A   H   S   T   L   V   G   R   V   R   V   A   E   G   A   I   V   R   -

GGGGGTCACACGTGGTGGGCCCGCTGCTGATCGGCCCGGGTGCCGTCGTCAGCAACTCCA
---------+---------+---------+---------+---------+---------+   3120
CCCCCAGTGTGCACCACCCGGGCGACCACTAGCCGCGCCCACGGCAGCAGTCGTTGAGGT
  G   S   H   V   V   G   P   V   V   I   G   A   G   A   V   V   S   N   S   S   -

GTGTCGGCCCGTACACCTCCATCGGGGAGGACTGCCGGGTCGAGGACAGCGCCATCGAGT
---------+---------+---------+---------+---------+---------+   3180
CACAGCCGGGCATGTGGAGGTAGCCCCTCCTGACGGCCCAGCTCCTGTCGCGGTAGCTCA
  V   G   P   Y   T   S   I   G   E   D   C   R   V   E   D   S   A   I   E   Y   -

ACTCCGTCCTGCTGCGCGGCGCCCAGGTCGAGGGGCGTCCCGCATCGAGGCGTCCCTCA
---------+---------+---------+---------+---------+---------+   3240
TGAGGCAGGACGACGCGCCGCGGGTCCAGCTCCCCCGCAGGGCGTAGCTCCGCAGGGAGT
  S   V   L   L   R   G   A   Q   V   E   C   A   S   R   I   E   A   S   L   I   -

TCGGCCGCGGCGCCGTCGTCGGCCCGGCCCCCCGTCTCCCGCAGGCTCACCGACTGGTGA
---------+---------+---------+---------+---------+---------+   3300
AGCCGGCGCCGCGGCAGCAGCCGGGCCGGGGGGCAGAGGGCGTCCGAGTGGCTGACCACT
  G   R   G   A   V   V   C   P   A   P   R   L   P   Q   A   H   R   L   V   I   -

TCGGCGACCACAGCAAGGTGTATCTCACCCCATGACCACGACCATCCTCGTCACCGGCGG
---------+---------+---------+---------+---------+---------+   3360
AGCCGCTGGTGTCGTTCCACATAGAGTGGGGTACTGGTGCTGGTAGGAGCAGTGGCCGCC
                                    M   T   T   T   I   L   V   T   G   G   -
  G   D   H   S   K   V   Y   L   T   P   *
                                    acbD ─────────

S
                                              m
                                              a
                                              I
AGCGGGCTTCATTCGCTCCGCCTACGTCCGCCGGCTCCTGTCGCCCGGGGCCCCCGGCGG
---------+---------+---------+---------+---------+---------+   3420
TCGCCCGAAGTAAGCGAGGCGGATGCAGGCGGCCGAGGACAGCGGGCCCCGGGGGCCGCC
  A   G   F   I   R   S   A   Y   V   R   R   L   L   S   P   G   A   P   G   G   -

CGTCGCGGTGACCGTCCTCGACAAACTCACCTACGCCGGCAGCCTCGCCCGCCTGCACGC
---------+---------+---------+---------+---------+---------+   3480
GCAGCGCCACTGGCAGGAGCTGTTTGAGTGGATGCGGCCGTCGGAGCGGGCGGACGTGCG
  V   A   V   T   V   L   D   K   L   T   Y   A   G   S   L   A   R   L   H   A   -

GGTGCGTGACCATCCCGGCCTCACCTTCGTCCAGGGCGACGTGTGCGACACCGCGCTCGT
---------+---------+---------+---------+---------+---------+   3540
CCACGCACTGGTAGGGCCGGAGTGGAAGCAGGTCCCGCTGCACACGCTGTGGCGCGAGCA
  V   R   D   H   P   G   L   T   F   V   Q   G   D   V   C   D   T   A   L   V   -

CGACACGCTGGCCGCGCGGCACGACGACATCGTGCACTTCGCGGCCGAGTCGCACGTCGA
---------+---------+---------+---------+---------+---------+   3600
GCTGTGCGACCGGCGCGCCGTGCTGCTGTAGCACGTGAAGCGCCGGCTCAGCGTGCAGCT
  D   T   L   A   A   R   H   D   D   I   V   H   F   A   A   E   S   H   V   D   -

CCGCTCCATCACCGACAGCGGTGCCTTCACCCGCACCAACGTGCTGGGCACCCAGGTCCT
---------+---------+---------+---------+---------+---------+   3660
GGCGAGGTAGTGGCTGTCGCCACGGAAGTGGGCGTGGTTGCACGACCCGTGGGTCCAGGA
  R   S   I   T   D   S   G   A   F   T   R   T   N   V   L   G   T   Q   V   L   -

GCTCGACGCCGCGCTCCGCCACGGTGTGCGCACCTTCGTGCACGTCTCCACCGACGAGGT
---------+---------+---------+---------+---------+---------+   3720
CGAGCTGCGGCGCGAGGCGGTGCCACACGCGTGGAAGCACGTGCAGAGGTGGCTGCTCCA
  L   D   A   A   L   R   H   G   V   R   T   F   V   H   V   S   T   D   E   V   -

GTACGGCTCCCTCCCGCACGGGGCCGCCGCGGAGAGCGACCCCCTGCTTCCGACCTCGCC
---------+---------+---------+---------+---------+---------+   3780
CATGCCGAGGGAGGGCGTGCCCCGGCGGCGCCTCTCGCTGGGGGACGAAGGCTGGAGCGG
  Y   G   S   L   P   H   G   A   A   A   E   S   D   P   L   L   P   T   S   P   -
```

TABLE 4-continued (SEQ ID NO.: 7, 8, 9, 10, 11, 12, 13)

```
GTACGCGGCGTCGAAGGCGGCCTCGGACCTCATGGCGCTCGCCCACCACCGCACCCACGG
---------+---------+---------+---------+---------+---------+  3840
CATGCGCCGCAGCTTCCGCCGGAGCCTGGAGTACCGCGAGCGGGTGGTGGCGTGGGTGCC
 Y  A  A  S  K  A  A  S  D  L  M  A  L  A  H  H  R  T  H  G   -

CCTGGACGTCCGGGTGACCCGCTGTTCGAACAACTTCGGCCCCCACCAGCATCCCGAGAA
---------+---------+---------+---------+---------+---------+  3900
GGACCTGCAGGCCCACTGGGCGACAAGCTTGTTGAAGCCGGGGGTGGTCGTAGGGCTCTT
 L  D  V  R  V  T  R  C  S  N  N  F  G  P  H  Q  H  P  E  K   -

GCTCATACCGCGCTTCCTGACCAGCCTCCTGTCCGGCGGCACCGTTCCCCTCTACGGCGA
---------+---------+---------+---------+---------+---------+  3960
CGAGTATGGCGCGAAGGACTGGTCGGAGGACAGGCCGCCGTGGCAAGGGGAGATGCCGCT
 L  I  P  R  F  L  T  S  L  L  S  G  G  T  V  P  L  Y  G  D   -

CGGGCGGCACGTGCGCGACTGGCTGCACGTCGACGACCACGTCAGGGCCGTCGAACTCGT
---------+---------+---------+---------+---------+---------+  4020
GCCCGCCGTGCACGCGCTGACCGACGTGCAGCTGCTGGTGCAGTCCCGGCAGCTTGAGCA
 G  R  H  V  R  D  W  L  H  V  D  D  H  V  R  A  V  E  L  V   -
                         B
                         g
                         l
                         I
                         I
CCGCGTGTCGGGCCGGCCGGGAGAGATCTACAACATCGGGGGCGGCACCTCGCTGCCCAA
---------+---------+---------+---------+---------+---------+  4080
GGCGCACAGCCCGGCCGGCCCTCTCTAGATGTTGTAGCCCCCGCCGTGGAGCGACGGGTT
 R  V  S  G  R  P  G  E  I  Y  N  I  G  G  G  T  S  L  P  N   -

S
       s
       t
       I
CCTGGAGCTCACGCACCGGTTGCTCGCACTGTGCGGCGCGGGCCCGGAGCGCATCGTCCA
---------+---------+---------+---------+---------+---------+  4140
GGACCTCGAGTGCGTGGCCAACGAGCGTGACACGCCGCGCCCGGGCCTCGCGTAGCAGGT
 L  E  L  T  H  R  L  L  A  L  C  G  A  G  P  E  R  I  V  H   -

CGTCGAGAACCGCAAGGGGCACGACCGGCGCTACGCGGTCGACCACAGCAAGATCACCGC
---------+---------+---------+---------+---------+---------+  4200
GCAGCTCTTGGCGTTCCCCGTGCTGGCCGCGATGCGCCAGCTGGTGTCGTTCTAGTGGCG
 V  E  N  R  K  G  H  D  R  R  Y  A  V  D  H  S  K  I  T  A   -
                      N
                      r
                      u
                      I
GGAACTCGGTTACCGGCCGCGCACCGACTTCGCGACCGCGCTGGCCGACACCGCGAAGTG
---------+---------+---------+---------+---------+---------+  4260
CCTTGAGCCAATGGCCGGCGCGTGGCTGAAGCGCTGGCGCGACCGGCTGTGGCGCTTCAC
 E  L  G  Y  R  P  R  T  D  F  A  T  A  L  A  D  T  A  K  W   -

GTACGAGCGGCACGAGGACTGGTGGCGTCCCCTGCTCGCCGCGACA<u>TGA</u>CGTCGGGCCGG
---------+---------+---------+---------+---------+---------+  4320
CATGCTCGCCGTGCTCCTGACCACCGCAGGGGACGAGCGGCGCTGTACTGCAGCCCGGCC
 Y  E  R  H  E  D  W  W  R  P  L  L  A  A  T  *

ACCGCAACCACCGGCCCCGGCCGGCACACCGCCGCCCGCGGCCGGTGGCCGGCCGGTCAG
---------+---------+---------+---------+---------+---------+  4380
TGGCGTTGGTGGCCGGGGCCGGCCGTGTGGCGGCGGGCGCCGGCCACCGGCCGGCCAGTC
                                                          *   -

CGTCCGTGAGCCGGGCGCCGGCCGCCCCGCGGGCCGGCGGCGGTGGACCCCCGGACCACC
---------+---------+---------+---------+---------+---------+  4440
GCAGGCACTCGGCCCGCGGCCGGCGGGGCGCCCGGCCGCCGCCACCTGGGGGCCTGGTGG
    R  G  H  A  P  R  R  G  G  R  P  G  A  A  T  S  G  R  V  V   -

E
               c
               o
               R
               I
AGTTCCGGCATGAAGACGAATTCGGTGCGCGGCGGCGGCGTTCCGCTCATCTCCTCCAGC
---------+---------+---------+---------+---------+---------+  4500
TCAAGGCCGTACTTCTGCTTAAGCCACGCGCCGCCGCCGCAAGGCGAGTAGAGGAGGTCG
    L  E  P  M  F  V  F  E  T  R  P  P  P  T  G  S  M  E  E  L   -
```

TABLE 4-continued (SEQ ID NO.: 7, 8, 9, 10, 11, 12, 13)

```
AGTGCGTCCACGGCGACCTGCCCCATCGCCTTGACGGGCTGTCTGATGGTGGTCAGGGGA
---------+---------+---------+---------+---------+---------+   4560
TCACGCAGGTGCCGCTGGACGGGGTAGCGGAACTGCCCGACAGACTACCACCAGTCCCCT
  L   A   D   V   A   V   Q   G   M   A   K   V   P   Q   R   I   T   T   L   P   -

GGGTCGGTGAAGGCCATGAGCGGCGAGTCGTCGAAGCCGACCACCGAGATGTCACCGGGA
---------+---------+---------+---------+---------+---------+   4620
CCCAGCCACTTCCGGTACTCGCCGCTCAGCAGCTTCGGCTGGTGGCTCTACAGTGGCCCT
  P   D   T   F   A   M   L   P   S   D   D   F   G   V   V   S   I   D   G   P   -

ACCGTGAGACCCCGCCGGCGCGCGGCCCGCACGGCGCCGAGGGCCATCATGTCGCTGGCG
---------+---------+---------+---------+---------+---------+   4680
TGGCACTCTGGGGCGGCCGCGCGCCGGGCGTGCCGCGGCTCCCGGTAGTACAGCGACCGC
  V   T   L   G   R   R   R   A   A   R   V   A   G   L   A   M   M   D   S   A   -

CACATGACGGCGGTGCAGCCCAGGTCGATCAGCGCGGACGCGGCGGCCTGGCCCCCCTCC
---------+---------+---------+---------+---------+---------+   4740
GTGTACTGCCGCCACGTCGGGTCCAGCTAGTCGCGCCTGCGCCGCCGGACCGGGGGGAGG
  C   M   V   A   T   C   G   L   D   I   L   A   S   A   A   A   Q   G   G   E   -
                                         S
                                         s
                                         t
                                         I

AGGGAGAACAGCGAGTGCTGCACGAGCTCCTCGGACTCCCGCGCCGACACTCCCAGGTGC
---------+---------+---------+---------+---------+---------+   4800
TCCCTCTTGTCGCTCACGACGTGCTCGAGGAGCCTGAGGGCGCGGCTGTGAGGGTCCACG
  L   S   F   L   S   H   Q   V   L   E   E   S   E   R   A   S   V   G   L   H   -

TCCCGCACGCCGGCCCGGAACCCCTCGATCTTCCGCTGCACCGGCACGAAGCGGGCGGGC
---------+---------+---------+---------+---------+---------+   4860
AGGGCGTGCGGCCGGGCCTTGGGGAGCTAGAAGGCGACGTGGCCGTGCTTCGCCCGCCCG
  E   R   V   G   A   R   F   G   E   I   K   R   Q   V   P   V   F   R   A   P   -

CCGACGGCGAGGCCGACGCGCTCGTGCCCAGCTCCGCCAGGTGCGCCACGGCCAGGCGC
---------+---------+---------+---------+---------+---------+   4920
GGCTGCCGCTCCGGCTGCGCGAGCACGGGTCGAGGCGGTCCACGCGGTGCCGGTCCGCG
  G   V   A   L   G   V   R   E   H   G   L   E   A   L   H   A   V   A   L   R   -

ATCGCGGCCCGGTCGTCCGGGGAGACGAAGGGTGCCTCGATCCGGGGCGAGAACCCGTTC
---------+---------+---------+---------+---------+---------+   4980
TAGCGCCGGGCCAGCAGGCCCCTCTGCTTCCCACGGAGCTAGGCCCCGCTCTTGGGCAAG
  M   A   A   R   D   D   P   S   V   F   P   A   E   I   R   P   S   F   G   N   -

ACGAGGACGAAGGGCACCTGCCGCTCGTGCAGCCGGCCGTACCGTCCGGTCTCGGCGGTG
---------+---------+---------+---------+---------+---------+   5040
TGCTCCTGCTTCCCGTGGACGGCGAGCACGTCGGCCGGCATGGCAGGCCAGAGCCGCCAC
  V   L   V   F   P   V   Q   R   E   H   L   R   G   Y   R   G   T   E   A   T   -

GTGTCCGCGTGCAGTCCGGAGACGAAGATGATGCCGGACACCCCGCGGTCCACGAGCATC
---------+---------+---------+---------+---------+---------+   5100
CACAGGCGCACGTCAGGCCTCTGCTTCTACTACGGCCTGTGGGGCGCCAGGTGCTCGTAG
  T   D   A   H   L   G   S   V   F   I   I   G   S   V   G   R   D   V   L   M   -
                                         S
                                         m
                                         a
                                         I
TCCGTGAGTTCGTCCTCGGTCGAGCCGCCCGGGGTCTGCGTGGCGAGCACGGGCGTGTAG
---------+---------+---------+---------+---------+---------+   5160
AGGCACTCAAGCAGGAGCCAGCTCGGCGGGCCCCAGACGCACCGCTCGTGCCCGCACATC
  E   T   L   E   D   E   T   S   G   G   P   T   Q   T   A   L   V   P   T   Y   -

CCCTGACGCGTGAGCGCCTGCCCCATCACCTGGGCCAGTGCGGGGAAGAAGGGGTTGTCC
---------+---------+---------+---------+---------+---------+   5220
GGGACTGCGCACTCGCGGACGGGGTAGTGGACCCGGTCACGCCCCTTCTTCCCCAACAGG
  G   Q   R   T   L   A   Q   G   M   V   Q   A   L   A   P   F   F   P   N   D   -

AGTTCGGGGGTGACCAGTCCGACCAGCTCGGCGCGGCGCTGTCGCGCCGGCTGCTCGTAG
---------+---------+---------+---------+---------+---------+   5280
TCAAGCCCCACTGGTCAGGCTGGTCGAGCCGCGCCGCGACAGCGCGGCCGACGAGCATC
  L   E   P   T   V   L   G   V   L   E   A   R   R   Q   R   A   P   Q   E   Y   -

CCCAGCGCGTCCAGTGCGGTCAGCACCGAGTCGCGGGTGCCGGTGGCCACACCGCGCGCA
---------+---------+---------+---------+---------+---------+   5340
GGGTCGCGCAGGTCACGCCAGTCGTGGCTCAGCGCCCACGGCCACCGGTGTGGCGCGCGT
  G   L   A   D   L   A   T   L   V   S   D   R   T   G   T   A   V   G   R   A   -
```

TABLE 4-continued (SEQ ID NO.: 7, 8, 9, 10, 11, 12, 13)

```
                                                    S
                                                    m
                                                    a
                                                    I
CCGTTCAGCACCCGGCTGACCGTGGCCTTGCTGACGCCCGCCCGGGCTGCGATGTCGGCG
---------+---------+---------+---------+---------+---------+   5400
GGCAAGTCGTGGGCCGACTGGCACCGGAACGACTGCGGGCGGGCCCGACGCTACAGCCGC
 G  N  L  V  R  S  V  T  A  K  S  V  G  A  R  A  A  I  D  A  -

AGCCGCATGGTCATGGCAACGCACTCTACCTGTCGGGGCGTCAGGGCGTGCCCACCGCGC
---------+---------+---------+---------+---------+---------+   5460
TCGGCGTACCAGTACCGTTGCGTGAGATGGACAGCCCCGCAGTCCCGCACGGGTGGCGCG
 L  R  M  T  M
          ──────── acbE
GCGGAACCGGCGGACTGCGGGGCACGGCCCGTCCGCCGCCCACGGACCACGCGCCCGAAA
---------+---------+---------+---------+---------+---------+   5520
CGCCTTGGCCGCCTGACGCCCCGTGCCGGGCAGGCGGCGGGTGCCTGGTGCGCGGGCTTT CGATGGCTGAAAATGCTTGCAGCAAATTGCCGCAACGTCTTTCGGCGGCTTTTCGATCCT
---------+---------+---------+---------+---------+---------+   5580
GCTACCGACTTTTACGAACGTCGTTTAACGGCGTTGCAGAAAGCCGCCGAAAAGCTAGGA GTTACGTTCCTGGCAACCCCGGCGCCGCGCAGAAGCGGTTGGCGTGAGGCGTCCAGACCT
---------+---------+---------+---------+---------+---------+   5640
CAATGCAAGGACCGTTGGGGCCGCGGCGCGTCTTCGCCAACCGCACTCCGCAGGTCTGGA CCGCCCGATTCCGGGATCACTCAGGGGAGTTCACAATGCGGCGTGGCATTGCGGCCACCG
---------+---------+---------+---------+---------+---------+   5700
GGCGGGCTAAGGCCCTAGTGAGTCCCCTCAAGTGTTACGCCGCACCGTAACGCCGGTGGC
                              M  R  R  G  I  A  A  T  A  -
acbF ────────
CGCTGTTCGCGGCTGTGGCCATGACGGCATCGGCGTGTGGCGGGGGCGACAACGGCGGAA
---------+---------+---------+---------+---------+---------+   5760
GCGACAAGCGCCGACACCGGTACTGCCGTAGCCGCACACCGCCCCCGCTGTTGCCGCCTT
  L  F  A  A  V  A  M  T  A  S  A  C  G  G  G  D  N  G  G  S  -

K
    p
    n
    I
GCGGTACCGACGCGGGCGGCACGGAGCTGTCGGGGACCGTCACCTTCTGGGACACGTCCA
---------+---------+---------+---------+---------+---------+   5820
CGCCATGGCTGCGCCCGCCGTGCCTCGACAGCCCCTGGCAGTGGAAGACCCTGTGCAGGT
  G  T  D  A  G  G  T  E  L  S  G  T  V  T  F  W  D  T  S  N  -

ACGAAGCCGAGAAGGCGACGTACCAGGCCCTCGCGGAGGGCTTCGAGAAGGAGCACCCGA
---------+---------+---------+---------+---------+---------+   5880
TGCTTCGGCTCTTCCGCTGCATGGTCCGGGAGCGCCTCCCGAAGCTCTTCCTCGTGGGCT
  E  A  E  K  A  T  Y  Q  A  L  A  E  G  F  E  K  E  H  P  K  -

AGGTCGACGTCAAGTACGTCAACGTCCCGTTCGGCGAGGCGAACGCCAAGTTCAAGAACG
---------+---------+---------+---------+---------+---------+   5940
TCCAGCTGCAGTTCATGCAGTTGCAGGGCAAGCCGCTCCGCTTGCGGTTCAAGTTCTTGC
  V  D  V  K  Y  V  N  V  F  F  G  E  A  N  A  K  F  K  N  A  -

CCGCGGGCGGCAACTCCGGTGCCCCGGACGTGATGCGCTACGGACCTCGCCTGGGTCGCGG
---------+---------+---------+---------+---------+---------+   6000
GGCGCCCGCCGTTGAGGCCACGGGGCCTGCACTACGCATGCCTCCAGCGGACCCAGCGCC
  A  G  G  N  S  G  A  P  D  V  M  R  T  E  V  A  W  V  A  D  -

ACTTCGCCAGCATCGGCTACCTCGCCCCGCTCGACGGCACGCCCGCCCTCGACGACGGGT
---------+---------+---------+---------+---------+---------+   6060
TGAAGCGGTCGTAGCCGATGGAGCGGGGCGAGCTGCCGTGCGGGCGGGAGCTGCTGCCCA
  F  A  S  I  G  Y  L  A  P  L  D  G  T  P  A  L  D  D  G  S  -

CGGACCACCTTCCCCAGGGCGGCAGCACCAGGTACGAGGGGAAGACCTACGCGGTCCCGC
---------+---------+---------+---------+---------+---------+   6120
GCCTGGTGGAAGGGGTCCCGCCGTCGTGGTCCATGCTCCCCTTCTGGATGCGCCAGGGCG
  D  H  L  P  Q  G  G  S  T  R  Y  E  G  K  T  Y  A  V  P  Q  -

AGGTGATCGACACCCTGGCGCTCTTCTACAACAAGGAACTGCTGACGAAGGCCGGTGTCG
---------+---------+---------+---------+---------+---------+   6180
TCCACTAGCTGTGGGACCGCGAGAAGATGTTGTTCCTTGACGACTGCTTCCGGCCACAGC
  V  I  D  T  L  A  L  F  Y  N  K  E  L  L  T  K  A  G  V  E  -
```

TABLE 4-continued (SEQ ID NO.: 7, 8, 9, 10, 11, 12, 13)

```
AGGTGCCGGGCTCCCTCGCCGAGCTGAAGACGGCCGCCGCCGAGATCACCGAGAAGACCG
---------+---------+---------+---------+---------+---------+   6240
TCCACGGCCCGAGGGAGCGGCTCGACTTCTGCCGGCGGCGGCTCTAGTGGCTCTTCTGGC
  V  P  G  S  L  A  E  L  K  T  A  A  A  E  I  T  E  K  T  G  -

GCGCGAGCGGCCTCTACTGCGGGGCGACGACCCGTACTTGGTTCCTGCCCTACCTCTACG
---------+---------+---------+---------+---------+---------+   6300
CGCGCTCGCCGGAGATGACGCCCCGCTGCTGGGCATGAACCAAGGACGGGATGGAGATGC
  A  S  G  L  Y  C  G  A  T  T  R  T  W  F  L  P  Y  L  Y  G  -

GGGAGGGCGGCGACCTGGTCGACGAGAAGAACAAGACCGTCACGGTCGACGACGAAGCCG
---------+---------+---------+---------+---------+---------+   6360
CCCTCCCGCCGCTGGACCAGCTGCTCTTCTTGTTCTGGCAGTGCCAGCTGCTGCTTCGGC
  E  G  G  D  L  V  D  E  K  N  K  T  V  T  V  D  D  E  A  G  -

GTGTGCGCGCCTACCGCGTCATCAAGGACCTCGTGGACAGCAAGGCGGCCATCACCGACG
---------+---------+---------+---------+---------+---------+   6420
CACACGCGCGGATGGCGCAGTAGTTCCTGGAGCACCTGTCGTTCCGCCGGTAGTGGCTGC
  V  R  A  Y  R  V  I  K  D  L  V  D  S  K  A  A  I  T  D  A  -

CGTCCGACGGCTGGAACAACATGCAGAACGCCTTCAAGTCGGGCAAGGTCGCCATGATGG
---------+---------+---------+---------+---------+---------+   6480
GCAGGCTGCCGACCTTGTTGTACGTCTTGCGGAAGTTCAGCCCGTTCCAGCGGTACTACC
  S  D  G  W  N  N  M  Q  N  A  F  K  S  G  K  V  A  M  M  V  -

TCAACGGCCCCTGGGCCATCGAGGACGTCAAGGCGGGAGCCCGCTTCAAGGACGCCGGCA
---------+---------+---------+---------+---------+---------+   6540
AGTTGCCGGGGACCCGGTAGCTCCTGCAGTTCCGCCCTCGGGCGAAGTTCCTGCGGCCGT
  N  G  P  W  A  I  E  D  V  K  A  G  A  R  F  K  D  A  G  N  -

ACCTGGGGGTCGCCCCCGTCCCGGCCGGCAGTGCCGGACAGGGCTCTCCCCAGGGCGGGT
---------+---------+---------+---------+---------+---------+   6600
TGGACCCCCAGCGGGGGCAGGGCCGGCCGTCACGGCCTGTCCCGAGAGGGGTCCCGCCCA
  L  G  V  A  P  V  P  A  G  S  A  G  Q  G  S  P  Q  G  G  W  -

GGAACCTCTCGGTGTACGCGGGCTCGAAGAACCTCGACGCCTCCTACGCCTTCGTGAAGT
---------+---------+---------+---------+---------+---------+   6660
CCTTGGAGAGCCACATGCGCCCGAGCTTCTTGGAGCTGCGGAGGATGCGGAAGCACTTCA
  N  L  S  V  Y  A  G  S  K  N  L  D  A  S  Y  A  F  V  K  Y  -

ACATGAGCTCCGCCAAGGTGCAGCAGCAGACCACCGAGAAGCTGAGCCTGCTGCCCACCC
---------+---------+---------+---------+---------+---------+   6720
TGTACTCGAGGCGGTTCCACGTCGTCGTCTGGTGGCTCTTCGACTCGGACGACGGGTGGG
  M  S  S  A  K  V  Q  Q  Q  T  T  E  K  L  S  L  L  P  T  R  -

GCACGTCCGTCTACGAGGTCCCGTCCGTCGCGGACAACGACATGGTGAAGTTCTTCAAGC
---------+---------+---------+---------+---------+---------+   6780
CGTGCAGGCAGATGCTCCAGGGCAGGCAGCGCCTGTTGCTCTACCACTTCAAGAAGTTCG
  T  S  V  Y  E  V  P  S  V  A  D  N  E  M  V  K  F  F  K  P  -

CGGCCGTCGACAAGGCCGTCGAACGGCCGTGGATCGCCGAGGGCAATGCCCTCTTCGAGC
---------+---------+---------+---------+---------+---------+   6840
GCCGGCAGCTGTTCCGGCAGCTTGCCGGCACCTAGCGGCTCCCGTTACGGGAGAAGCTCG
  A  V  D  K  A  V  E  R  P  W  I  A  E  G  N  A  L  F  E  P  -

P
           s
           t
           I
CGATCCGGCTGCAG
---------+----                                                   6854
GCTAGGCCGACGTC
  I  R  L  Q                                                    -
```

What is claimed is:

1. An isolated polynucleotide comprising a nucleotide sequence which encodes a protein for biosynthesizing acarbose, wherein said nucleotide sequence is capable of hybridizing under stringent conditions with the sequence of SEQ ID No: 7.

2. A polynucleotide according to claim 1, wherein said polynucleotide comprises a nucleotide sequence encoding a protein for biosynthesizing acarbose and homologous pseudo-oligosaccharides.

3. A polynucleotide according to claim 1, wherein said polynucleotide comprises six open reading frames which encode six proteins, and wherein said six open reading frames are arranged, with respect to their direction of transcription and order, as acbA, acbB, acbC, acbD, acbE and acbF depicted in FIG. 3.

4. A polynucleotide according to claim 3, wherein said polynucleotide has a restriction enzyme cleavage site pattern as depicted in FIG. 3.

5. An isolated polynucleotide comprising a nucleotide sequence encoding at least one protein for biosynthesizing acarbose, wherein said nucleotide sequence is selected from the group consisting of:

(a) a nucleotide sequence of SEQ ID No: 7;

(b) a nucleotide sequence which is capable of hybridizing, under stringent conditions, with the sequence of SEQ ID No: 7;

(c) a nucleotide sequence consisting of nucleotide 1 to 720 of SEQ ID No: 7;

(d) a nucleotide sequence consisting of nucleotides 720 to 2006 of SEQ ID No: 7;

(e) a nucleotide sequence consisting of nucleotides 2268 to 3332 of SEQ ID No: 7;

(f) a nucleotide sequence consisting of nucleotides 3332 to 4306 of SEQ ID No: 7;

(g) a nucleotide sequence consisting of nucleotides 4380 to 5414 of SEQ ID No: 7;

(h) a nucleotide sequence consisting of nucleotides 5676 to 6854 of SEQ ID No: 7;

(i) a nucleotide sequence which is capable of hybridizing, under stringent conditions, with the sequence according to (a), (b), (c), (d) (e), (f), (g) or (h); and (j) a nucleotide sequence which, because of the degeneracy of the genetic code, differs from the nucleotide sequence according to (a), (b), (c), (d), (e), (f), (g) (h) and (i), but which permits the expression of any protein which can be expressed using the nucleotide sequence of (a), (b), (c), (d), (e), (f), (g), (h) and (i), respectively.

6. A polynucleotide according to claim 5, comprising a nucleotide sequence consisting of nucleotides 1 to 720 of SEQ ID No: 7.

7. A polynucleotide according to claim 5, comprising a nucleotide sequence consisting of nucleotides 720 to 2006 of SEQ ID No: 7.

8. A polynucleotide according to claim 5, comprising a nucleotide sequence consisting of nucleotides 2268 to 3332 of SEQ ID No: 7.

9. A polynucleotide according to claim 5, comprising a nucleotide sequence consisting of nucleotides 3332 to 4306 of SEQ ID No: 7.

10. A polynucleotide according to claim 5, comprising a nucleotide sequence consisting of nucleotides 4380 to 5414 of SEQ ID No: 7.

11. A polynucleotide according to claim 5, comprising a nucleotide sequence consisting of nucleotides 5676 to 6854 of SEO ID No: 7.

12. Oligonucleotide primer for the PCR amplification of the polynucleotide according to claim 5, consisting of fragments of SEQ ID No: 7.

13. Oligonucleotide primer according to claim 12, wherein said primer is selected from the nucleotide sequences of SEQ ID No: 1 and SEQ ID No: 2.

14. Vector, which comprises a polynucleotide according to claim 1.

15. Vector according to claim 14, comprising a promoter operatively linked to a polynucleotide encoding an antisense strand of the polynucleotide of claim 1.

16. Vector according to claim 14, which is an expression vector and said polynucleotide is linked operatively to a promoter sequence.

17. Vector according to claim 16, which is suitable for expression in host organisms which are selected from the group consisting of E. coli strains, Bacillus subtilis strains, Streptomyces strains, Actinoplanes strains, Ampullanrella strains, Streptosporangium strains, Streptomyces hygroscopicus var. limoneus, Streptomyces glaucescens, Aspergillus niger, Penicillium chrysogenum and Saccharomyces cerevisae.

18. Vector according to claim 16, which is suitable for expression in Streptomyces glaucescens GLA.O or Actinoplanes sp.

19. Host cell which is transformed with a polynucleotide according to claim 1 or a vector according to claim 14.

20. Host cell according to claim 19, which is selected from the group consisting of E. coli strains, Bacillus subtilis strains, Streptomyces strains, Actinoplanes strains, Ampullariella strains, Streptosporangium strains, Streptomyces hygroscopicus var. limoneus, Streptomyces glaucescens, Aspergillus niger, Penicillium chrysogenum and Saccharomyces cerevisiae.

21. Host cell according to claim 20, which is selected from the group consisting of Streptomyces glaucescens GLA.O and Actinoplanes sp.

22. A process for obtaining a protein for biosynthesizing acarbose, comprising:

(a) introducing the polynucleotide according to claim 1 into a suitable host cell; and (b) isolating the expression product of the polynucleotide.

23. Process according to claim 22, wherein the host cell is selected from the group consisting of E. coli strains, Bacillus subtilis strains, Streptomyces strains, Actinoplanes strains, Ampullariella strains, Streptosporangium strains, Streptomyces hygroscopicus var. limoneus or Streptomyces glaucescens, Aspergillus niger, Penicillium chrysogenum and Saccharomyces cerevisiae.

24. Process according to claim 22, wherein the host cell is selected from the group consisting of Streptomyces glaucescens GLA.O and Actinoplanes sp.

25. An isolated polynucleotide comprising a nucleotide sequence encoding a protein for biosynthesizing acarbose, wherein said nucleotide sequence is capable of hybridizing, under stringent conditions, with a nucleotide sequence selected from the group consisting of a nucleotide sequence consisting of nucleotides 1 to 720 of SEQ ID NO: 7, a nucleotide sequence consisting of nucleotides 720 to 2006 of SEQ ID NO: 7, a nucleotide sequence consisting of nucleotides 2268 to 3332 of SEQ ID NO: 7, a nucleotide sequence consisting of nucleotides 3332 to 4306 of SEQ ID NO: 7, a nucleotide sequence consisting of nucleotides 4380 to 5414 of SEQ ID NO: 7, and a nucleotide sequence consisting of nucleotides 5676 to 6854 of SEQ ID NO: 7.

26. An isolated polynucleotide according to claim 1, wherein said nucleotide sequence comprises at least 100 consecutive nucleotide residues of SEQ ID No: 7.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "Primer"

(xi) SEQUENCE DESCRIPTION: SEQ ID NO:1:

```
CSGGSGSSGC SGGSTTCATS GG                                          22
```

(2) INFORMATION FOR SEQ ID NO:2:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "Primer"

(xi) SEQUENCE DESCRIPTION: SEQ ID NO:2:

```
GGGWVCTGGY VSGGSCCGTA GTTG                                        24
```

(2) INFORMATION FOR SEQ ID NO:3:

(i) SEQUENCE CHARACTERISTICS:
       (A) LENGTH: 546 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:3:

```
CCCGGGCGGG GCGGGGTTCA TCGGCTCCGC CTACGTCCGC CGGCTCCTGT CGCCCGGGGC   60

CCCCGGCGGC GTCGCGGTGA CCGTCCTCGA CAAACTCACC TACGCCGGCA GCCTCGCCCG  120

CCTGCACGCG GTGCGTGACC ATCCCGGCCT CACCTTCGTC CAGGGCGACG TGTGCGACAC  180

CGCGCTCGTC GACACGCTGG CCGCGCGGCA CGACGACATC GTGCACTTCG CGGCCGAGTC  240

GCACGTCGAC CGCTCCATCA CCGACAGCGG TGCCTTCACC CGCACCAACG TGCTGGGCAC  300

CCAGGTCCTG CTCGACGCCG CGCTCCGCCA CGGTGTGCGC ACCCTCGTGC ACGTCTCCAC  360

CGACGAGGTG TACGGCTCCC TCCCGCACGG GGCCGCCGCG GAGAGCGACC CCCTGCTCCC  420

GACCTCGCCG TACGCGGCGT CGAAGGCGGC CTCGGACCTC ATGGCGCTCG CCCACCACCG  480

CACCCACGGC CTGGACGTCC GGGTGACCCG CTGTTCGAAC AACTACGGCC CGCACCAGTT  540

CCCGGG                                                            546
```

-continued (2) INFORMATION FOR SEQ ID NO:4:

(i) SEQUENCE CHARACTERISTICS:
        (A) LENGTH: 541 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
CCCCGGGTGC TGGTAGGGGC CGTAGTTGTT GGAGCAGCGG GTGATGCGCA CGTCCAGGCC      60
GTGGCTGACG TGCATGGCCA GCGCGAGCAG GTCGCCCGAC GCCTTGGAGG TGGCATAGGG     120
GCTGTTGGGG CGCAGCGGCT CGTCCTCCGT CCACGACCCC GTCTCCAGCG AGCCGTAGAC     180
CTCGTCGGTG GACACCTGCA CGAAGGGGGC CACGCCGTGC CGCAGGGCCG CGTCGAGGAG     240
TGTCTGCGTG CCGCCGGCGT TGGTCCGCAC GAACGCGGCG GCATCGAGCA GCGAGCGGTC     300
CACGTGCGAC TCGGCGGCGA GGTGCACGAC CTGGTCCTGG CCGGCCATGA CCCGGTCGAC     360
CAGGTCCGCG TCGCAGATGT CGCCGTGGAC GAAGCGCAGC CGGGGGTGGT CGCGGACCGG     420
GTCGAGGTTG GCGAGGTTGC CGGCGTAGCT CAGGGCGTCG AGCACGGTGA CGACGGCGTC     480
GGGCGGCCCG TCCGGACCGA GGAGGGTGCG GACGTAGTGC GAGCCCATGA ACCCCGCCGC     540
C                                                                     541
```

(2) INFORMATION FOR SEQ ID NO:5:

(i) SEQUENCE CHARACTERISTICS:
        (A) LENGTH: 180 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:5:

```
Ala Ala Gly Phe Met Gly Ser His Tyr Val Arg Thr Leu Leu Gly Pro
1               5                   10                  15

Asp Gly Pro Pro Asp Ala Val Val Thr Val Leu Asp Ala Leu Ser Tyr
            20                  25                  30

Ala Gly Asn Leu Ala Asn Leu Asp Pro Val Arg Asp His Pro Arg Leu
        35                  40                  45

Arg Phe Val His Gly Asp Ile Cys Asp Ala Asp Leu Val Asp Arg Val
    50                  55                  60

Met Ala Gly Gln Asp Gln Val Val His Leu Ala Ala Glu Ser His Val
65                  70                  75                  80

Asp Arg Ser Leu Leu Asp Ala Ala Phe Val Arg Thr Asn Ala Gly
            85                  90                  95

Gly Thr Gln Thr Leu Leu Asp Ala Ala Leu Arg His Gly Val Ala Pro
        100                 105                 110

Phe Val Gln Val Ser Thr Asp Glu Val Tyr Gly Ser Leu Glu Thr Gly
        115                 120                 125

Ser Trp Thr Glu Asp Glu Pro Leu Arg Pro Asn Ser Pro Tyr Ala Thr
    130                 135                 140

Ser Lys Ala Ser Gly Asp Leu Leu Ala Leu Ala Met His Val Ser His
145                 150                 155                 160
```

```
Gly Leu Asp Val Arg Ile Thr Arg Cys Ser Asn Asn Tyr Gly Pro Tyr
                165                 170                 175
Gln His Pro Gly
            180
```

(2) INFORMATION FOR SEQ ID NO:6:

(i) SEQUENCE CHARACTERISTICS:
        (A) LENGTH: 181 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:6:

```
Pro Gly Gly Ala Gly Phe Ile Gly Ser Ala Tyr Val Arg Arg Leu Leu
1               5                   10                  15
Ser Pro Gly Ala Pro Gly Gly Val Ala Val Thr Val Leu Asp Lys Leu
                20                  25                  30
Thr Tyr Ala Gly Ser Leu Ala Arg Leu His Ala Val Arg Asp His Pro
            35                  40                  45
Gly Leu Thr Phe Val Gln Gly Asp Val Cys Asp Thr Ala Leu Val Asp
    50                  55                  60
Thr Leu Ala Ala Arg His Asp Asp Ile Val His Phe Ala Ala Glu Ser
65                  70                  75                  80
His Val Asp Arg Ser Ile Thr Asp Ser Gly Ala Phe Thr Arg Thr Asn
                85                  90                  95
Val Leu Gly Thr Gln Val Leu Leu Asp Ala Ala Leu Arg His Gly Val
                100                 105                 110
Arg Thr Leu Val His Val Ser Thr Asp Glu Val Tyr Gly Ser Leu Pro
            115                 120                 125
His Gly Ala Ala Ala Glu Ser Asp Pro Leu Leu Pro Thr Ser Pro Tyr
    130                 135                 140
Ala Ala Ser Lys Ala Ala Ser Asp Leu Met Ala Leu Ala His Arg
145                 150                 155                 160
Thr His Gly Leu Asp Val Arg Val Thr Arg Cys Ser Asn Asn Tyr Gly
                165                 170                 175
Pro His Gln Phe Pro
            180
```

(2) INFORMATION FOR SEQ ID NO:7:

(i) SEQUENCE CHARACTERISTICS:
        (A) LENGTH: 6854 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
CTGCAGGGTT CCCTGGTGCA CGACCCGCCC CTGGTCGACG ACCAGGGCGC TGTCGCAGAT    60

CGCGGCGATG TCGGCGATGT CGTGGCTGGT GAGCACCACG GTGGTGCCCA GTTCCCGGTG   120

GGCGCGGTTG ACCAGCCGGC GCACCGCGTC CTTCAGCACC ATGTCGAGGC CGATCGTGGG   180

CTCGTCCCAG AACAGCACGG CCGGGTCGTG CAGCAGGCTC GCCGCGATCT CGGCGCGCAT   240

GCGCTGTCCG AGGCTGAGCT GCCGCACGGG GGTGGACCCC AGCGCGTCGA TGTCGAGGAG   300

GTCCCGGAAC AGGGCGAGGT TGCGCCGGTA GACCGGTCCG GGGATGTCGT AGATGCGGCG   360
```

```
CAGGATGCGG AAGGAGTCGG GTACCGACAG GTCCCACCAG AGCTGGCTGC GCTGGCCGAA    420

GACGACGCCG ATCGTGCGGG CGTTGCGCTG CCGGTGCCGG TAGGGCTCCA GCCCGGCGAC    480

CGTGCAGCGG CCGGAGGTGG GGGTCATGAT GCCGGTCAGC ATCTTGATCG TGGTCGACTT    540

GCCGGCTCCG TTGGCGCCGA TGTAGGCGGT CTTCGTGCCG GCCGGTATCT CGAAGGAGAC    600

GTCGTCGACG GCGCGCACGA CGCGGTACCG GCGGGTCAGG AGGGTGGAGA GGCTGCCGAG    660

CAGGCCGGGC TCGCGTTCGG CCAGCCGGAA CTCCTTGACG AGGTGTTCGG CCACGATCAC    720

GCGATCACCC GCTCGACGGC CGTCTCCAGC AGGCGCAGGC CCTCGTCGAG CAGCGCCTCG    780

TCGAGGGTGA ACGGCGGTGC CAGCCGCAGG ATGTGGCCGC CCAGGGAGGT GCGCAGCCCC    840

AGGTCGAGGG CGGTGGTGTA GACGGCCCGG GCGGTCTCGG GGGCGGGTGC CCGGCCGACG    900

GCGTCGGTGA CGAACTCCAG GCCCCACAGC AGTCCGAGGC CGCGTACCTG GCCGAGCTGG    960

GGGAAGCGGG ACTCCAGGGC GCGCAGCCGC TCCTGGATGA GCTCGCCGAG GACGCGCACG    1020

CGGTCGATCA GCCGGTCGCG CTCGACGACC TCCAGCGTGG CGCGGGCGGC GGCGATCCCC    1080

AGTGGGTTGC TCGCGTACGT CGAGGCGTAC GCCCCGGGGT GGCCGCCTCC GGCCTGCGCA    1140

GCTTCCGCGC GTCCGGCCAG CACGGCGAAG GGGAATCCGC TCGCGGTGCC CTTGGACAGC    1200

ATCGCCAGGT CCGGCTCGAT GCCGAACAGT TCGCTGGCGA GGAAGGCGCC GGTGCGCCCG    1260

CCGCCGGTGA GGACCTCGTC GGCGACGAGC AGCACGCCGC CGTCCCGGCA GGCGCCGGCG    1320

ATCCGCTCCC AGTAGCCGGG GGGCGGCACG ATGACGCCTG CCGCGCCGAG GACGGGTTCG    1380

AAGACCAGGG CCGAGACGTT GGGCTTCTCC GCGATGTGCC GGCGCACGAG GGTCGCGCAC    1440

CGCACGTCGC ACGAGGGGTA CTCCAGGCCC AGGGGACAGC GGTAGCCAGT AGGGGCTGTA    1500

GCCAGCACGC TGTTGCCGCT GAAGGCCTGG TGGCCGATGT CCCAGTGGAC CAGCATCCGG    1560

GCGCCCATGG TCTTGCCGTG GAAGCCGTGG CGCAGGGCGC AGATCCGGTT GCGGCCCGGC    1620

GCGGCGGTCG CCTGGACGAC CCGCAGGGCG GCCTCGACCA CCTCCGCGCC GGTGGAGAAG    1680

AAGGCGTAGG TGTCGAGCTG TTCGGGCAGC AGCCTGGCGA GCAGTTCCAG CAGGCCGGCG    1740

CGGTCCGGCC TGGCGCTGTC GTGGACGTTC ACAGGCGGC GGGCCTGGGT GGTGAGTGCC     1800

TCGACGACCT CCGGGTGCCC GTGGCCCAGT GACTGGGTGA GGGTCCCGGC CGCGAAGTCG    1860

AGGTACTGGT TGCCGTCCAG GTCGGTCAGA ACGGGACCGC GTCCCTCGGC GAAGACCCGG    1920

CGTCCGTGGA CGGCTTCCTC GGAGGCGCCC GGCGCCAGGT GGCGGGCCTC CCGTGCCAGG    1980

TGCTGTGTCT GCCGTAAGCC TGTCATCGCT GCCTCTGCTC GTCGGACCGG CTGACGCGAT    2040

CGCCGGCGAA CTGCGTTGTG GCGCACCACG GTTGGGCGG CTCGGCGCTG AGTCAAACAC     2100

TTGAACACAC ACCGCTGCAA GAGTTTGCGG GTTGTTTCAG AAAGTTGTTG CGAGCGGCCC    2160

CGGCACTCTG GTTGAGTCGA CGTGCTTACG GCGCCACCAC GCCTCACGTT CGAGGAGGGA    2220

CCTGTGAGAA CAAGCCCGCA GACCGACCCG CTCCCGCGGA GGCCGAGGTG AAGGCCCTGG    2280

TCCTGGCAGG TGGAACCGGC AGCAGACTGA GGCCGTTCAC CCACACCGCC GCCAAGCAGC    2340

TGCTCCCCAT CGCCAACAAG CCCGTGCTCT TCTACGCGCT GGAGTCCCTC GCCGCGGCGG    2400

GTGTCCGGGA GGCCGGCGTC GTCGTGGGCG CGTACGGCCG GGAGATCCGC GAACTCACCG    2460

GCGACGGCAC CGCGTTCGGG TTACGCATCA CCTACCTCCA CCAGCCCCGC CCGCTCGGTC    2520

TCGCGCACGC GGTGCGCATC GCCCGCGGCT TCCTGGGCGA CGACGACTTC CTGCTGTACC    2580

TGGGGGACAA CTACCTGCCC CAGGGCGTCA CCGACTTCGC CCGCCAATCG GCCGCCGATC    2640

CCGCGGCGGC CCGGCTGCTG CTCACCCCGG TCGCGGACCC GTCCGCCTTC GGCGTCGCGG    2700

AGGTCGACGC GGACGGGAAC GTGCTGCGCT TGGAGGAGAA ACCCGACGTC CCGCGCAGCT    2760
```

```
CGCTCGCGCT CATCGGCGTG TACGCCTTCA GCCCGGCCGT CCACGAGGCG GTACGGGCCA   2820

TCACCCCCTC CGCCCGCGGC GAGCTGGAGA TCACCCACGC CGTGCAGTGG ATGATCGACC   2880

GGGGCCTGCG CGTACGGGCC GAGACCACCA CCCCGGCCCTG GCGCGACACC GGCAGCGCGG   2940

AGGACATGCT GGAGGTCAAC CGTCACGTCC TGGACGGACT GGAGGGCCGC ATCGAGGGGA   3000

AGGTCGACGC GCACAGCACG CTGGTCGGCC GGGTCCGGGT GGCCGAAGGC GCGATCGTGC   3060

GGGGGTCACA CGTGGTGGGC CCGGTGGTGA TCGGCGCGGG TGCCGTCGTC AGCAACTCCA   3120

GTGTCGGCCC GTACACCTCC ATCGGGGAGG ACTGCCGGGT CGAGGACAGC GCCATCGAGT   3180

ACTCCGTCCT GCTGCGCGGC GCCCAGGTCG AGGGGCGTC CCGCATCGAG GCGTCCCTCA   3240

TCGGCCGCGG CGCCGTCGTC GGCCCGGCCC CCGTCTCCC GCAGGCTCAC CGACTGGTGA   3300

TCGGCGACCA CAGCAAGGTG TATCTCACCC CATGACCACG ACCATCCTCG TCACCGGCGG   3360

AGCGGGCTTC ATTCGCTCCG CCTACGTCCG CCGGCTCCTG TCGCCCGGG CCCCCGGCGG   3420

CGTCGCGGTG ACCGTCCTCG ACAAACTCAC CTACGCCGGC AGCCTCGCCC GCCTGCACGC   3480

GGTGCGTGAC CATCCCGGCC TCACCTTCGT CCAGGGCGAC GTGTGCGACA CCGCGCTCGT   3540

CGACACGCTG GCCGCGCGGC ACGACGACAT CGTGCACTTC GCGGCCGAGT CGCACGTCGA   3600

CCGCTCCATC ACCGACAGCG GTGCCTTCAC CCGCACCAAC GTGCTGGGCA CCCAGGTCCT   3660

GCTCGACGCC GCGCTCCGCC ACGGTGTGCG CACCTTCGTG CACGTCTCCA CCGACGAGGT   3720

GTACGGCTCC CTCCCGCACG GGGCCGCCGC GGAGAGCGAC CCCCTGCTTC CGACCTCGCC   3780

GTACGCGGCG TCGAAGGCGG CCTCGGACCT CATGGCGCTC GCCCACCACC GCACCCACGG   3840

CCTGGACGTC CGGGTGACCC GCTGTTCGAA CAACTTCGGC CCCCACCAGC ATCCCGAGAA   3900

GCTCATACCG CGCTTCCTGA CCAGCCTCCT GTCCGGCGGC ACCGTTCCCC TCTACGGCGA   3960

CGGGCGGCAC GTGCGCGACT GGCTGCACGT CGACGACCAC GTCAGGGCCG TCGAACTCGT   4020

CCGCGTGTCG GGCCGGCCGG GAGAGATCTA CAACATCGGG GCGGCACCT CGCTGCCCAA   4080

CCTGGAGCTC ACGCACCGGT TGCTCGCACT GTGCGGCGCG GGCCCGGAGC GCATCGTCCA   4140

CGTCGAGAAC CGCAAGGGGC ACGACCGGCG CTACGCGGTC GACCACAGCA AGATCACCGC   4200

GGAACTCGGT TACCGGCCGC GCACCGACTT CGCGACCGCG CTGGCCGACA CCGCGAAGTG   4260

GTACGAGCGG CACGAGGACT GGTGGCGTCC CCTGCTCGCC GCGACATGAC GTCGGGCCGG   4320

ACCGCAACCA CCGGCCCCGG CCGGCACACC GCCGCCCGCG GCCGGTGGCC GGCCGGTCAG   4380

CGTCCGTGAG CCGGGCGCCG GCCGCCCCGC GGGCCGGCGG CGGTGGACCC CCGGACCACC   4440

AGTTCCGGCA TGAAGACGAA TTCGGTGCGC GGCGGCGGCG TTCCGCTCAT CTCCTCCAGC   4500

AGTGCGTCCA CGGCGACCTG CCCCATCGCC TTGACGGGCT GTCTGATGGT GGTCAGGGGA   4560

GGGTCGGTGA AGGCCATGAG CGGCGAGTCG TCGAAGCCGA CCACCGAGAT GTCACCGGGA   4620

ACCGTGAGAC CCCGCCGGCG CGCGGCCCGC ACGGCGCCGA GGGCCATCAT GTCGCTGGCG   4680

CACATGACGG CGGTGCAGCC CAGGTCGATC AGCGCGGACG CGGCGGCCTG GCCCCCCTCC   4740

AGGGAGAACA GCGAGTGCTG CACGAGCTCC TCGGACTCCC GCGCCGACAC TCCCAGGTGC   4800

TCCCGCACGC CGGCCCGGAA CCCCTCGATC TTCCGCTGCA CCGGCACGAA GCGGGCGGGC   4860

CCGACGGCGA GGCCGACGCG CTCGTGCCCC AGCTCCGCCA GGTGCGCCAC GGCCAGGCGC   4920

ATCGCGGCCC GGTCGTCCGG GGAGACGAAG GGTGCCTCGA TCCGGGGCGA GAACCCGTTC   4980

ACGAGGACGA AGGGCACCTG CCGCTCGTGC AGCCGGCCGT ACCGTCCGGT CTCGGCGGTG   5040

GTGTCCGCGT GCAGTCCGGA GACGAAGATG ATGCCGGACA CCCCGCGGTC CACGAGCATC   5100

TCCGTGAGTT CGTCCTCGGT CGAGCCGCCC GGGGTCTGCG TGGCGAGCAC GGGCGTGTAG   5160
```

```
CCCTGACGCG TGAGCGCCTG CCCCATCACC TGGGCCAGTG CGGGGAAGAA GGGGTTGTCC    5220

AGTTCGGGGG TGACCAGTCC GACCAGCTCG GCGCGGCGCT GTCGCGCCGG CTGCTCGTAG    5280

CCCAGCGCGT CCAGTGCGGT CAGCACCGAG TCGCGGGTGC CGGTGGCCAC ACCGCGCGCA    5340

CCGTTCAGCA CCCGGCTGAC CGTGGCCTTG CTGACGCCCG CCCGGGCTGC GATGTCGGCG    5400

AGCCGCATGG TCATGGCAAC GCACTCTACC TGTCGGGGCG TCAGGGCGTG CCCACCGCGC    5460

GCGGAACCGG CGGACTGCGG GGCACGGCCC GTCCGCCGCC CACGGACCAC GCGCCCGAAA    5520

CGATGGCTGA AAATGCTTGC AGCAAATTGC CGCAACGTCT TCGGCGGCT TTTCGATCCT     5580

GTTACGTTCC TGGCAACCCC GGCGCCGCGC AGAAGCGGTT GGCGTGAGGC GTCCAGACCT    5640

CCGCCCGATT CCGGGATCAC TCAGGGGAGT TCACAATGCG GCGTGGCATT GCGGCCACCG    5700

CGCTGTTCGC GGCTGTGGCC ATGACGGCAT CGGCGTGTGG CGGGGCGAC AACGGCGGAA     5760

GCGGTACCGA CGCGGGCGGC ACGGAGCTGT CGGGGACCGT CACCTTCTGG GACACGTCCA    5820

ACGAAGCCGA GAAGGCGACG TACCAGGCCC TCGCGGAGGG CTTCGAGAAG GAGCACCCGA    5880

AGGTCGACGT CAAGTACGTC AACGTCCCGT TCGGCGAGGC GAACGCCAAG TTCAAGAACG    5940

CCGCGGGCGG CAACTCCGGT GCCCCGGACG TGATGCGTAC GGAGGTCGCC TGGGTCGCGG    6000

ACTTCGCCAG CATCGGCTAC CTCGCCCCGC TCGACGGCAC GCCCGCCCTC GACGACGGGT    6060

CGGACCACCT TCCCCAGGGC GGCAGCACCA GGTACGAGGG GAAGACCTAC GCGGTCCCGC    6120

AGGTGATCGA CACCCTGGCG CTCTTCTACA CAAGGAACT GCTGACGAAG GCCGGTGTCG     6180

AGGTGCCGGG CTCCCTCGCC GAGCTGAAGA CGGCCGCCGC CGAGATCACC GAGAAGACCG    6240

GCGCGAGCGG CCTCTACTGC GGGGCGACGA CCCGTACTTG GTTCCTGCCC TACCTCTACG    6300

GGGAGGGCGG CGACCTGGTC GACGAGAAGA ACAAGACCGT CACGGTCGAC GACGAAGCCG    6360

GTGTGCGCGC CTACCGCGTC ATCAAGGACC TCGTGGACAG CAAGGCGGCC ATCACCGACG    6420

CGTCCGACGG CTGGAACAAC ATGCAGAACG CCTTCAAGTC GGGCAAGGTC GCCATGATGG    6480

TCAACGGCCC CTGGGCCATC GAGGACGTCA AGGCGGGAGC CCGCTTCAAG GACGCCGGCA    6540

ACCTGGGGGT CGCCCCCGTC CCGGCCGGCA GTGCCGGACA GGGCTCTCCC CAGGGCGGGT    6600

GGAACCTCTC GGTGTACGCG GGCTCGAAGA ACCTCGACGC CTCCTACGCC TTCGTGAAGT    6660

ACATGAGCTC CGCCAAGGTG CAGCAGCAGA CCACCGAGAA GCTGAGCCTG CTGCCCACCC    6720

GCACGTCCGT CTACGAGGTC CCGTCCGTCG CGGACAACGA GATGGTGAAG TTCTTCAAGC    6780

CGGCCGTCGA CAAGGCCGTC GAACGGCCGT GGATCGCCGA GGGCAATGCC CTCTTCGAGC    6840

CGATCCGGCT GCAG                                                      6854
```

(2) INFORMATION FOR SEQ ID NO:8:

(i) SEQUENCE CHARACTERISTICS:
        (A) LENGTH: 240 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:8:

```
Val Ile Val Ala Glu His Leu Val Lys Glu Phe Arg Leu Ala Glu Arg
 1               5                  10                  15

Glu Pro Gly Leu Leu Gly Ser Leu Ser Thr Leu Leu Thr Arg Arg Tyr
            20                  25                  30

Arg Val Val Arg Ala Val Asp Val Ser Phe Glu Ile Pro Ala Gly
        35                  40                  45
```

```
Thr Lys Thr Ala Tyr Ile Gly Ala Asn Gly Ala Gly Lys Ser Thr Thr
 50                  55                  60

Ile Lys Met Leu Thr Gly Ile Met Thr Pro Thr Ser Gly Arg Cys Thr
 65                  70                  75                  80

Val Ala Gly Leu Glu Pro Tyr Arg His Arg Gln Arg Asn Ala Arg Thr
                 85                  90                  95

Ile Gly Val Val Phe Gly Gln Arg Ser Gln Leu Trp Trp Asp Leu Ser
                100                 105                 110

Val Pro Asp Ser Phe Arg Ile Leu Arg Arg Ile Tyr Asp Ile Pro Gly
                115                 120                 125

Pro Val Tyr Arg Arg Asn Leu Ala Leu Phe Arg Asp Leu Leu Asp Ile
    130                 135                 140

Asp Ala Leu Gly Ser Thr Pro Val Arg Gln Leu Ser Leu Gly Gln Arg
145                 150                 155                 160

Met Arg Ala Glu Ile Ala Ala Ser Leu Leu His Asp Pro Ala Val Leu
                165                 170                 175

Phe Trp Asp Glu Pro Thr Ile Gly Leu Asp Met Val Leu Lys Asp Ala
                180                 185                 190

Val Arg Arg Leu Val Asn Arg Ala His Arg Glu Leu Gly Thr Thr Val
    195                 200                 205

Val Leu Thr Ser His Asp Ile Ala Asp Ile Ala Ala Ile Cys Asp Ser
    210                 215                 220

Ala Leu Val Val Asp Gln Gly Arg Val Val His Gln Gly Thr Leu Gln
225                 230                 235                 240

(2) INFORMATION FOR SEQ ID NO:9:

(i) SEQUENCE CHARACTERISTICS:
        (A) LENGTH: 429 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:9:

Met Thr Gly Leu Arg Gln Thr Gln His Leu Ala Arg Glu Ala Arg His
 1               5                  10                  15

Leu Ala Pro Gly Ala Ser Glu Glu Ala Val His Gly Arg Arg Val Phe
                 20                  25                  30

Ala Glu Gly Arg Gly Pro Val Leu Thr Asp Leu Asp Gly Asn Gln Tyr
             35                  40                  45

Leu Asp Phe Ala Ala Gly Thr Leu Thr Gln Ser Leu Gly His Gly His
 50                  55                  60

Pro Glu Val Val Glu Ala Leu Thr Thr Gln Ala Arg Arg Leu Trp Asn
 65                  70                  75                  80

Val His Asp Ser Ala Thr Pro Asp Arg Ala Gly Leu Leu Glu Leu Leu
                 85                  90                  95

Ala Arg Leu Leu Pro Glu Gln Leu Asp Thr Tyr Ala Phe Phe Ser Thr
                100                 105                 110

Gly Ala Glu Val Val Glu Ala Ala Leu Arg Val Gln Ala Thr Ala
            115                 120                 125

Ala Pro Gly Arg Asn Arg Ile Cys Ala Leu Arg His Gly Phe His Gly
    130                 135                 140

Lys Thr Met Gly Ala Arg Met Leu Val Trp Asp Ile Gly His Gln
145                 150                 155                 160
```

```
Ala Phe Ser Gly Asn Ser Val Leu Ala Thr Ala Pro Thr Gly Tyr Arg
                165                 170                 175

Cys Pro Leu Gly Leu Glu Tyr Pro Ser Cys Asp Val Arg Cys Ala Thr
                180                 185                 190

Leu Val Arg Arg His Ile Ala Glu Lys Pro Asn Val Ser Ala Leu Val
                195                 200                 205

Phe Glu Pro Val Leu Gly Ala Ala Gly Val Ile Val Pro Pro Pro Gly
    210                 215                 220

Tyr Trp Glu Arg Ile Ala Gly Ala Cys Arg Asp Gly Val Leu Leu
225                 230                 235                 240

Val Ala Asp Glu Val Leu Thr Gly Gly Arg Thr Gly Ala Phe Leu
                245                 250                 255

Ala Ser Glu Leu Phe Gly Ile Glu Pro Asp Leu Ala Met Leu Ser Lys
                260                 265                 270

Gly Thr Ala Ser Gly Phe Pro Phe Ala Val Leu Ala Gly Arg Ala Glu
                275                 280                 285

Ala Ala Gln Ala Gly Gly Gly His Pro Gly Ala Tyr Ala Ser Thr Tyr
                290                 295                 300

Ala Ser Asn Pro Leu Gly Ile Ala Ala Arg Ala Thr Leu Glu Val
305                 310                 315                 320

Val Glu Arg Asp Arg Leu Ile Asp Arg Val Arg Val Leu Gly Glu Leu
                325                 330                 335

Ile Gln Glu Arg Leu Arg Ala Leu Glu Ser Arg Phe Pro Gln Leu Gly
                340                 345                 350

Gln Val Arg Gly Leu Gly Leu Leu Trp Gly Leu Glu Phe Val Thr Asp
                355                 360                 365

Ala Val Gly Arg Ala Pro Ala Pro Glu Thr Ala Arg Ala Val Tyr Thr
    370                 375                 380

Thr Ala Leu Asp Leu Gly Leu Arg Thr Ser Leu Gly Gly His Ile Leu
385                 390                 395                 400

Arg Leu Ala Pro Pro Phe Thr Leu Asp Glu Ala Leu Leu Asp Glu Gly
                405                 410                 415

Leu Arg Leu Leu Glu Thr Ala Val Glu Arg Val Ile Ala
                420                 425
```

(2) INFORMATION FOR SEQ ID NO:10:

(i) SEQUENCE CHARACTERISTICS:
        (A) LENGTH: 355 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:10:

```
Val Lys Ala Leu Val Leu Ala Gly Gly Thr Gly Ser Arg Leu Arg Pro
1               5                   10                  15

Phe Thr His Thr Ala Ala Lys Gln Leu Leu Pro Ile Ala Asn Lys Pro
                20                  25                  30

Val Leu Phe Tyr Ala Leu Glu Ser Leu Ala Ala Ala Gly Val Arg Glu
                35                  40                  45

Ala Gly Val Val Val Gly Ala Tyr Gly Arg Glu Ile Arg Glu Leu Thr
    50                  55                  60

Gly Asp Gly Thr Ala Phe Gly Leu Arg Ile Thr Tyr Leu His Gln Pro
65                  70                  75                  80
```

-continued

```
Arg Pro Leu Gly Leu Ala His Ala Val Arg Ile Ala Arg Gly Phe Leu
                85                  90                  95
Gly Asp Asp Phe Leu Leu Tyr Leu Gly Asp Asn Tyr Leu Pro Gln
            100                 105                 110
Gly Val Thr Asp Phe Ala Arg Gln Ser Ala Ala Asp Pro Ala Ala Ala
            115                 120                 125
Arg Leu Leu Leu Thr Pro Val Ala Asp Pro Ser Ala Phe Gly Val Ala
        130                 135                 140
Glu Val Asp Ala Asp Gly Asn Val Leu Arg Leu Glu Lys Pro Asp
145                 150                 155                 160
Val Pro Arg Ser Ser Leu Ala Leu Ile Gly Val Tyr Ala Phe Ser Pro
                165                 170                 175
Ala Val His Glu Ala Val Arg Ala Ile Thr Pro Ser Ala Arg Gly Glu
            180                 185                 190
Leu Glu Ile Thr His Ala Val Gln Trp Met Ile Asp Arg Gly Leu Arg
        195                 200                 205
Val Arg Ala Glu Thr Thr Thr Arg Pro Trp Arg Asp Thr Gly Ser Ala
210                 215                 220
Glu Asp Met Leu Glu Val Asn Arg His Val Leu Asp Gly Leu Glu Gly
225                 230                 235                 240
Arg Ile Glu Gly Lys Val Asp Ala His Ser Thr Leu Val Gly Arg Val
                245                 250                 255
Arg Val Ala Glu Gly Ala Ile Val Arg Gly Ser His Val Val Gly Pro
            260                 265                 270
Val Val Ile Gly Ala Gly Ala Val Ser Asn Ser Ser Val Gly Pro
        275                 280                 285
Tyr Thr Ser Ile Gly Glu Asp Cys Arg Val Glu Asp Ser Ala Ile Glu
        290                 295                 300
Tyr Ser Val Leu Leu Arg Gly Ala Gln Val Glu Gly Ala Ser Arg Ile
305                 310                 315                 320
Glu Ala Ser Leu Ile Gly Arg Gly Ala Val Val Gly Pro Ala Pro Arg
                325                 330                 335
Leu Pro Gln Ala His Arg Leu Val Ile Gly Asp His Ser Lys Val Tyr
            340                 345                 350
Leu Thr Pro
        355

(2) INFORMATION FOR SEQ ID NO:11:

(i) SEQUENCE CHARACTERISTICS:
        (A) LENGTH: 325 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:11:

Met Thr Thr Thr Ile Leu Val Thr Gly Gly Ala Gly Phe Ile Arg Ser
1               5                   10                  15
Ala Tyr Val Arg Arg Leu Leu Ser Pro Gly Ala Pro Gly Gly Val Ala
            20                  25                  30
Val Thr Val Leu Asp Lys Leu Thr Tyr Ala Gly Ser Leu Ala Arg Leu
        35                  40                  45
His Ala Val Arg Asp His Pro Gly Leu Thr Phe Val Gln Gly Asp Val
    50                  55                  60
```

```
Cys Asp Thr Ala Leu Val Asp Thr Leu Ala Ala Arg His Asp Ile
 65                  70                  75                  80

Val His Phe Ala Ala Glu Ser His Val Asp Arg Ser Ile Thr Asp Ser
                 85                  90                  95

Gly Ala Phe Thr Arg Thr Asn Val Leu Gly Thr Gln Val Leu Leu Asp
                100                 105                 110

Ala Ala Leu Arg His Gly Val Arg Thr Phe Val His Val Ser Thr Asp
                115                 120                 125

Glu Val Tyr Gly Ser Leu Pro His Gly Ala Ala Glu Ser Asp Pro
130                 135                 140

Leu Leu Pro Thr Ser Pro Tyr Ala Ala Ser Lys Ala Ala Ser Asp Leu
145                 150                 155                 160

Met Ala Leu Ala His Arg Thr His Gly Leu Asp Val Arg Val Thr
                165                 170                 175

Arg Cys Ser Asn Asn Phe Gly Pro His Gln His Pro Glu Lys Leu Ile
                180                 185                 190

Pro Arg Phe Leu Thr Ser Leu Leu Ser Gly Gly Thr Val Pro Leu Tyr
                195                 200                 205

Gly Asp Gly Arg His Val Arg Asp Trp Leu His Val Asp Asp His Val
210                 215                 220

Arg Ala Val Glu Leu Val Arg Val Ser Gly Arg Pro Gly Glu Ile Tyr
225                 230                 235                 240

Asn Ile Gly Gly Gly Thr Ser Leu Pro Asn Leu Glu Leu Thr His Arg
                245                 250                 255

Leu Leu Ala Leu Cys Gly Ala Gly Pro Glu Arg Ile Val His Val Glu
                260                 265                 270

Asn Arg Lys Gly His Asp Arg Arg Tyr Ala Val Asp His Ser Lys Ile
                275                 280                 285

Thr Ala Glu Leu Gly Tyr Arg Pro Arg Thr Asp Phe Ala Thr Ala Leu
                290                 295                 300

Ala Asp Thr Ala Lys Trp Tyr Glu Arg His Glu Asp Trp Trp Arg Pro
305                 310                 315                 320

Leu Leu Ala Ala Thr
                325

(2) INFORMATION FOR SEQ ID NO:12:

(i) SEQUENCE CHARACTERISTICS:
        (A) LENGTH: 345 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:12:

Met Thr Met Arg Leu Ala Asp Ile Ala Ala Arg Ala Gly Val Ser Lys
 1               5                  10                  15

Ala Thr Val Ser Arg Val Leu Asn Gly Ala Arg Gly Val Ala Thr Gly
                 20                  25                  30

Thr Arg Asp Ser Val Leu Thr Ala Leu Asp Ala Leu Gly Tyr Glu Gln
                 35                  40                  45

Pro Ala Arg Gln Arg Arg Ala Glu Leu Val Gly Leu Val Thr Pro Glu
 50                  55                  60

Leu Asp Asn Pro Phe Phe Pro Ala Leu Ala Gln Val Met Gly Gln Ala
 65                  70                  75                  80
```

```
Leu Thr Arg Gln Gly Tyr Thr Pro Val Leu Ala Thr Gln Thr Pro Gly
                85                  90                  95

Gly Ser Thr Glu Asp Glu Leu Thr Glu Met Leu Val Asp Arg Gly Val
                100                 105                 110

Ser Gly Ile Ile Phe Val Ser Gly Leu His Ala Asp Thr Thr Ala Glu
                115                 120                 125

Thr Gly Arg Tyr Gly Arg Leu His Glu Arg Gln Val Pro Phe Val Leu
                130                 135                 140

Val Asn Gly Phe Ser Pro Arg Ile Glu Ala Pro Phe Val Ser Pro Asp
145                 150                 155                 160

Asp Arg Ala Ala Met Arg Leu Ala Val Ala His Leu Ala Glu Leu Gly
                165                 170                 175

His Glu Arg Val Gly Leu Ala Val Gly Pro Ala Arg Phe Val Pro Val
                180                 185                 190

Gln Arg Lys Ile Glu Gly Phe Arg Ala Gly Val Arg Glu His Leu Gly
                195                 200                 205

Val Ser Ala Arg Glu Ser Glu Glu Leu Val Gln His Ser Leu Phe Ser
                210                 215                 220

Leu Glu Gly Gly Gln Ala Ala Ser Ala Leu Ile Asp Leu Gly Cys
225                 230                 235                 240

Thr Ala Val Met Cys Ala Ser Asp Met Met Ala Leu Gly Ala Val Arg
                245                 250                 255

Ala Ala Arg Arg Arg Gly Leu Thr Val Pro Gly Asp Ile Ser Val Val
                260                 265                 270

Gly Phe Asp Asp Ser Pro Leu Met Ala Phe Thr Asp Pro Pro Leu Thr
                275                 280                 285

Thr Ile Arg Gln Pro Val Lys Ala Met Gly Gln Val Ala Val Asp Ala
                290                 295                 300

Leu Leu Glu Glu Met Ser Gly Thr Pro Pro Arg Thr Glu Phe Val
305                 310                 315                 320

Phe Met Pro Glu Leu Val Val Arg Gly Ser Thr Ala Ala Gly Pro Arg
                325                 330                 335

Gly Gly Arg Arg Pro Ala His Gly Arg
                340                 345

(2) INFORMATION FOR SEQ ID NO:13:

(i) SEQUENCE CHARACTERISTICS:
        (A) LENGTH: 393 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:13:

Met Arg Arg Gly Ile Ala Ala Thr Ala Leu Phe Ala Ala Val Ala Met
1               5                   10                  15

Thr Ala Ser Ala Cys Gly Gly Gly Asp Asn Gly Ser Gly Thr Asp
                20                  25                  30

Ala Gly Gly Thr Glu Leu Ser Gly Thr Val Thr Phe Trp Asp Thr Ser
                35                  40                  45

Asn Glu Ala Glu Lys Ala Thr Tyr Gln Ala Leu Ala Glu Gly Phe Glu
50                  55                  60

Lys Glu His Pro Lys Val Asp Val Lys Tyr Val Asn Val Pro Phe Gly
65                  70                  75                  80
```

-continued

```
Glu Ala Asn Ala Lys Phe Lys Asn Ala Ala Gly Gly Asn Ser Gly Ala
                85              90              95

Pro Asp Val Met Arg Thr Glu Val Ala Trp Val Ala Asp Phe Ala Ser
            100             105             110

Ile Gly Tyr Leu Ala Pro Leu Asp Gly Thr Pro Ala Leu Asp Asp Gly
        115             120             125

Ser Asp His Leu Pro Gln Gly Gly Ser Thr Arg Tyr Glu Gly Lys Thr
    130             135             140

Tyr Ala Val Pro Gln Val Ile Asp Thr Leu Ala Leu Phe Tyr Asn Lys
145             150             155             160

Glu Leu Leu Thr Lys Ala Gly Val Glu Val Pro Gly Ser Leu Ala Glu
                165             170             175

Leu Lys Thr Ala Ala Ala Glu Ile Thr Glu Lys Thr Gly Ala Ser Gly
            180             185             190

Leu Tyr Cys Gly Ala Thr Thr Arg Thr Trp Phe Leu Pro Tyr Leu Tyr
        195             200             205

Gly Glu Gly Gly Asp Leu Val Asp Glu Lys Asn Lys Thr Val Thr Val
    210             215             220

Asp Asp Glu Ala Gly Val Arg Ala Tyr Arg Val Ile Lys Asp Leu Val
225             230             235             240

Asp Ser Lys Ala Ala Ile Thr Asp Ala Ser Asp Gly Trp Asn Asn Met
                245             250             255

Gln Asn Ala Phe Lys Ser Gly Lys Val Ala Met Met Val Asn Gly Pro
            260             265             270

Trp Ala Ile Glu Asp Val Lys Ala Gly Ala Arg Phe Lys Asp Ala Gly
        275             280             285

Asn Leu Gly Val Ala Pro Val Pro Ala Gly Ser Ala Gly Gln Gly Ser
    290             295             300

Pro Gln Gly Gly Trp Asn Leu Ser Val Tyr Ala Gly Ser Lys Asn Leu
305             310             315             320

Asp Ala Ser Tyr Ala Phe Val Lys Tyr Met Ser Ser Ala Lys Val Gln
                325             330             335

Gln Gln Thr Thr Glu Lys Leu Ser Leu Leu Pro Thr Arg Thr Ser Val
            340             345             350

Tyr Glu Val Pro Ser Val Ala Asp Asn Glu Met Val Lys Phe Phe Lys
        355             360             365

Pro Ala Val Asp Lys Ala Val Glu Arg Pro Trp Ile Ala Glu Gly Asn
370             375             380

Ala Leu Phe Glu Pro Ile Arg Leu Gln
385             390
```